(12) United States Patent
Zhang et al.

(10) Patent No.: US 11,041,184 B2
(45) Date of Patent: Jun. 22, 2021

(54) MYCOBACTERIOPHAGES CAPABLE OF DELIVERING AUTO-LUMINESCENT ELEMENTS AND USES THEREOF

(71) Applicant: GUANGZHOU INSTITUTES OF BIOMEDICINE AND HEALTH, CHINESE ACADEMY OF SCIENCES, Guangdong (CN)

(72) Inventors: Tianyu Zhang, Guangdong (CN); Zhiyong Liu, Guangdong (CN)

(73) Assignee: Guangzhou Institutes of Biomedicine and Health, Chinese Academy of Sciences, Guangzhou (CN)

( * ) Notice: Subject to any disclaimer, the term of this patent is extended or adjusted under 35 U.S.C. 154(b) by 139 days.

(21) Appl. No.: 16/124,252

(22) Filed: Sep. 7, 2018

(65) Prior Publication Data
US 2019/0040445 A1 Feb. 7, 2019

Related U.S. Application Data

(63) Continuation of application No. PCT/CN2016/081202, filed on May 6, 2016.

(30) Foreign Application Priority Data

Mar. 7, 2016 (CN) .......................... 201610127984.9

(51) Int. Cl.
| | | |
|---|---|---|
| C12Q 1/18 | (2006.01) |
| C12Q 1/04 | (2006.01) |
| C12N 15/10 | (2006.01) |
| C12N 15/73 | (2006.01) |
| C12Q 1/689 | (2018.01) |
| C12Q 1/70 | (2006.01) |
| C12N 15/70 | (2006.01) |
| C12N 15/74 | (2006.01) |
| C12Q 1/02 | (2006.01) |

(52) U.S. Cl.
CPC .......... *C12Q 1/18* (2013.01); *C12N 15/1034* (2013.01); *C12N 15/1037* (2013.01); *C12N 15/70* (2013.01); *C12N 15/73* (2013.01); *C12N 15/74* (2013.01); *C12Q 1/025* (2013.01); *C12Q 1/04* (2013.01); *C12Q 1/689* (2013.01); *C12Q 1/70* (2013.01); *G01N 2333/35* (2013.01)

(58) Field of Classification Search
CPC .. C12N 7/00; C12N 15/1034; C12N 15/1037; C12N 15/70; C12N 15/74; C12N 2795/00021; C12N 14/74; C12Q 1/025; C12Q 1/04; C12Q 1/18; C12Q 1/689; C12Q 1/70; G01N 2333/35
See application file for complete search history.

(56) References Cited

U.S. PATENT DOCUMENTS

| | | | | |
|---|---|---|---|---|
| 8,619,257 B2* | 12/2013 | Plowman | ........... | A61K 49/0013 356/432 |
| 2007/0185016 A1* | 8/2007 | Muir | ...................... | C07K 14/31 514/2.7 |
| 2012/0052292 A1* | 3/2012 | Pulapura | ................. | A61P 17/02 428/336 |
| 2014/0370495 A1* | 12/2014 | Jacobs | ................... | C12N 15/74 435/5 |

FOREIGN PATENT DOCUMENTS

| | | |
|---|---|---|
| CN | 1884555 A | 12/2006 |
| CN | 102719471 B | 10/2013 |
| WO | 2010097411 A1 | 9/2010 |

OTHER PUBLICATIONS

Nathalie Franche, Manon Vinay, Mireille Ansaldi. Substrate-independent luminescent phage-based biosensor to specifically detect enteric bacteria such as *E. coli*. Feb. 23, 2016. Springer. 24: 42-51. (Year: 2016).*
Seongmi Kim, Minsik Kim, and Sangryeol Ryu. Development of an Engineered Bioluminescent Reporter Phage for the Sensitive Detection of Viable *Salmonella* Typhimurium. May 8, 2014. ACS Publications. 86, 5858-5864 (Year: 2014).*
Tianyu Zhang, Si-Yang Li, Eric L. Nuermberger. Autoluminescent *Mycobacterium tuberculosis* for Rapid, Real-Time, Non-Invasive Assessment of Drug and Vaccine Efficacy. Jan. 2012. PLoS ONE. vol. 7. pp. 1-8 (Year: 2012).*
Francesca Forti, Veronica Mauri, Gianni Deho, Daniela Ghisotti. Isolation of conditional expression mutants in *Mycobacterium tuberculosis* by transposon mutagenesis. 2011. vol. 91. 569-578. (Year: 2011).*
William Jacobs, Gene Transfer in *Mycobacterium tuberculosis*: Shuttle Phasmids to Enlightenment. Apr. 11, 2014, American Society for Microbiology Press, vol. 2, pp. 1-22 (Year: 2014).*
Jain et al., Specialized Transduction Designed for Precise High-Throughput Unmarked Deletions in *Mycobacterium tuberculosis*, Jun. 3, 2014, mBio, vol. 5, 1-9 (Year: 2014).*
Jacobs WR et al.,"Rapid assessment of drug susceptibilities of *Mycobacterium tuberculosis* by means of luciferase reporter phages",Science,vol. 260,No. 5109,May 7, 1993.

(Continued)

*Primary Examiner* — Neil P Hammell

(57) ABSTRACT

A mycobacteriophage capable of delivering an auto-luminescent element includes luxCDABE genes for auto-luminescence of a host bacterium. The auto-luminescent element is located on a transposon, and can be randomly inserted into the host genome with the transposon. The mycobacteriophage can be used for rapid detection of a live host bacterium in a sample and detection of sensitivity of the host bacterium to a drug or drug combination.

2 Claims, 13 Drawing Sheets

Figure 1:
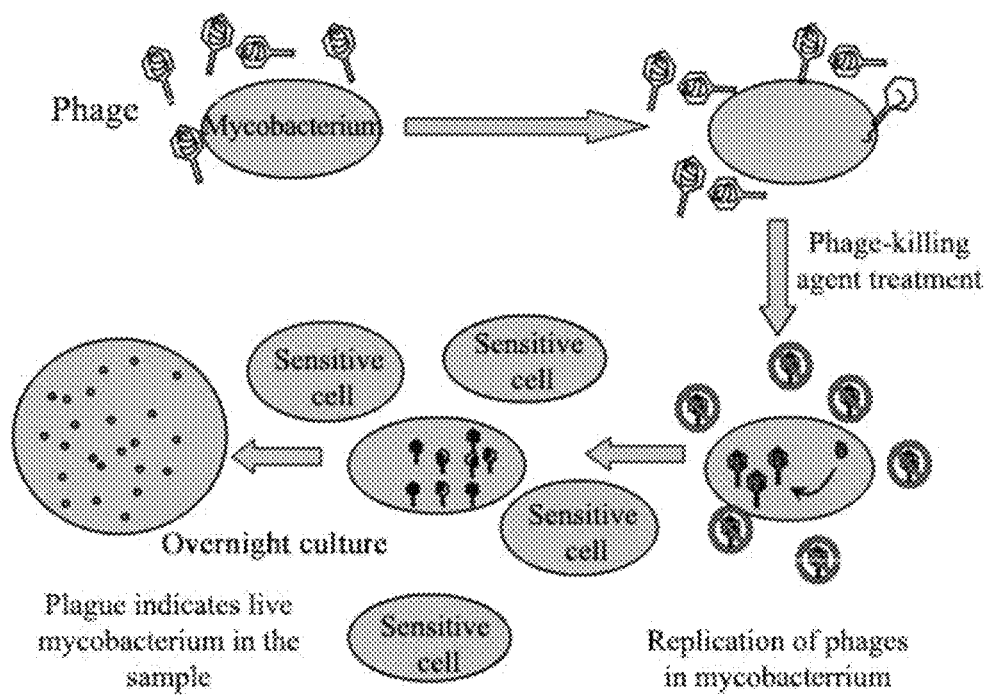

Specification includes a Sequence Listing.

(56) References Cited

OTHER PUBLICATIONS

Huang, Hairong et al., "Application of Phages in *Mycobacterium tuberculosis* Research", Chinese Journal of Tuberculosis and Respiratory Diseases, vol. 25, No. 8, Aug. 12, 2002.

Feng, Yang et al., "Engineering more stable, selectable marker-free autoluminescent mycobacteria by one step", PLOS One, 2015.

Tianyu Zhang et al., "Autoluminescent *Mycobacterium tuberculosis* for rapid, real-time, non-invasive assessment of drug and vaccine efficacy", PLOS One,2012.
Gyanu Lamichhane et al.,"A postgenomic method for predicting essential genes at subsaturation levels of mutagenesis: Application to *Mycobacterium tuberculosis*",Proc Natl Acad Sci USA,2003.
Shu-Chi Chang et al.,"Flow cytometric detection and quantification of mycobacteria in metalworking fluids",Int Biodeterior Biodegradation,2004.
McCann Jr et al.,"Beta-lactamase can function as a reporter of bacterial protein export during *Mycobacterium tuberculosis* infection of host cells",Microbiol SGM,2007.
Mochammad Hatta et al.,"Detection and identification of mycobacteria in sputum from suspected tuberculosis patients",BMC Res Notes,2010.
Danica Helb et al.,"Rapid detection of *Mycobacterium tuberculosis* and rifampin resistance by use of on-demand,near-patient technology",J Clin Microbiol,2010.
Garg SK et al.,"Diagnosis of tuberculosis: available technologies, limitations, and possibilities",J Clin Lab Anal,2003.
Hsieh SC et al.,"Rapid identification of *Mycobacterium tuberculosis* infection by a new array format-based surface plasmon resonance method",Nano scale Res Lett,2012.
Wilson SM et al.,"Evaluation of a new rapid bacteriophage-based method for the drug susceptibility testing of *Mycobacterium tuberculosis*",Nat Med,1997.
Mariana Piuri et al.,"Fluoromycobacteriophages for Rapid, Specific,and Sensitive Antibiotic Susceptibility Testing of *Mycobacterium tuberculosis*",PLOS One,2009.
Rondon L et al.,"Evaluation of fluoromycobacteriophages for detecting drug resistance in *Mycobacterium tuberculosis*", J Clin Microbiol,2011.
Agustina I. de la Iglesia et al.,"Comparison of the performances of two in-house rapid methods for antitubercular drug susceptibility testing",Antimicrob Agents Chemother,2009.
Francesca Forti et al.,"Isolation of conditional expression mutants in *Mycobacterium tuberculosis* by transposon mutagenesis. Tuberculosis",Tuberculosis,2011.
Xia Yu et al.,"Evaluation of Loop-mediated isothermal amplification for the rapid detection of *M. tuberculosis* in sputa", Chin J Lab Diagn,2013.
K. Lily Therese et al.; "Detection of *Mycobacterium tuberculosis* directly from sputum specimens & phenotypic drug resistance pattern of *M. tuberculosis* isolates from suspected tuberculosis patients in Chennai"; 2012. 135(5):778-782.
J. A. Robledo et al; "Evaluation of a rapid culture method for tuberculosis diagnosis: a Latin American multi-center study" 2006. 10(60):613-619.
L. Heifets, T. Linder, T. Sanchez, et al.; "Two Liquid Medium Systems, Mycobacteria Growth Indicator Tube and MB Redox Tube, for *Mycobacterium tuberculosis* Isolation from Sputum Specimens". Indian J Med Sci. 2012.135(5):778-782.
Tan, Yaoju et al; "Clinical application of phage bioassay for detection of *Mycobacterium tuberculosis* in sputum"; Chinese Journal of Laboratory Medicine; 2011. 34 (5):448-450.

* cited by examiner

MYCOBACTERIOPHAGES CAPABLE OF DELIVERING AUTO-LUMINESCENT ELEMENTS AND USES THEREOF

CROSS-REFERENCE TO RELATED APPLICATIONS

This application is a continuation of International patent Application No. PCT/CN2016/081202, filed on May 6, 2016, which claims the benefit of priority from Chinese Application No. 201610127984.9, filed on Mar. 7, 2016. The content of the aforementioned applications, including any intervening amendments thereto, are incorporated herein by reference.

TECHNICAL FIELD

The present invention relates to mycobacteriophages capable of delivering a set of auto-luminescent elements and uses thereof.

BACKGROUND OF THE PRESENT INVENTION

Mycobacterium is a type of organism that is slender and slightly curved, sometimes with branches or filamentum. Mycobacterium is a genus of Actinobacteria in taxonomy. Actinobacteria that are pathogenic to humans may or may not contain mycolic acids, and Mycobacterium contains mycolic acids. Such genus with no flagella or spores generally does not produce endotoxin or exotoxin, and its pathogenicity is related to the composition of bacteria. Mycobacterium causes chronic diseases accompanied by granulomas. A variety of mycobacteria mainly fall into three types, Mycobacterium tuberculosis complex, Mycobacterium leprae and non-tuberculous Mycobacterium (NTM). NTM can be divided into four groups according to colony pigmentation and growth rate. Group IV are bacteria of fast growing which grows fast at 25-45° C., and colonies are visible within 5-7 days of culture. The colonies are usually rough and some can produce pigments. Mycobacterium smegmatis (M. smegmatis) is one of them but does not produce pigments.

A variety of mycobacteria can cause diseases, and Mycobacterium tuberculosis (Mtb) is a pathogen causing tuberculosis. Mtb can invade various organs of the human body, and in particular, lungs. Tuberculosis remains an important infectious disease bringing about the largest number of deaths caused by a single pathogen. There are about 10 million new cases of tuberculosis each year worldwide (9.6 million and 10.4 million in 2014 and in 2016, respectively), and the death toll is about 1.8 million. In recent years, the emergence of drug-resistant tuberculosis has made the treatment of tuberculosis more difficult. Mtb grows very slowly. Generally it takes 3-5 weeks for Mtb to form visible colonies on plates. Therefore, the routine diagnosis of tuberculosis by culturing live Mtb is very time consuming, which takes about 4-8 weeks. Similarly, test on Mtb's sensitivity to a drug also takes a long time. It takes another 4-8 weeks to obtain the drug sensitivity results upon the growth of bacteria. In recent years, BD's MGIT 960 system has been most commonly used in clinical laboratories, shortening the time of diagnosis to 5 to 45 days and drug susceptibility testing to 8-12 days, which is still relatively long. The instrument and tubes for detection are large in size that it not only takes up much space, but also is expensive, and is not suitable for detecting many concentrations of a drug in high-throughput pattern. Therefore, it would be a great improvement to the treatment of tuberculosis if live Mtb in the clinical samples and their phenotypic sensitivity of various drugs in several concentrations are detected in a more rapid, convenient and economic way with improved specificity and accuracy.

The applicant has placed a set of auto-luminescent elements, LuxCDABE genes onto a mycobacterial integrating vector, and inserted it into the genome of Mtb, Mycobacterium Bacille Calmette-Guerin (BCG) or M. smegmatis. Several novel, selectable marker-free auto-luminescent mycobacteria that have lost the resistance marker gene were obtained (Patent No. ZL 201210183007.2); and the related article has been published[1]. Previous research has indicated that the auto-luminescence system can distinguish between dead and live bacteria, and the luminescence intensity of the bacteria is highly correlated with the number of bacteria. The constructed auto-luminescent bacteria can be used for in vitro drug screening, and can even be conveniently used for the detection of drugs and vaccines in vivo in mice, with surprising effect[2].

However, the delivery of such luminescent element is inefficient, and requires specialized equipments such as those for electrotransformation, as well as a large amount of Mtb of competent cells. Even if the transformation is successful, the luminescent bacteria require a growth time of about 4 weeks for growing up and another 1 to 2 weeks for the next step, such as drug sensitivity test. Therefore, it is impossible to rapidly detect live mycobacteria in a sample and drug sensitivity of wild Mtb (including laboratorial strains and clinically acquired strains) with the ability to deliver auto-luminescent elements to Mtb and other mycobacteria in a quick, simple and timely manner. To this end, it is desirable to carry a reporter element into mycobacteria such as Mtb through a phage.

Phage is a type of virus that is exclusively hosted by bacteria. Like other viruses, phages have their genetic material wrapped in a protein shell. Most phages also have a "tail" that is used to "inject" genetic material into the host. Mycobacteriophage can specifically recognize mycobacterium and use them as hosts. Phasmid is constructed from a plasmid vector and a phage vector, combining a replication origin of plasmid and phage elements. Thus, its replication can be carried out as a normal double-stranded plasmid molecule in Escherichia coli cells to generate double-stranded DNA. When the phasmid enters the host bacterium (for example, mycobacterium), the DNA and capsid protein of the progeny phages can be synthesized in the host bacterium. Under certain conditions, some of the phages are packaged into phage particles and are then released by lysing host cells, for example, temperature-sensitive auto-luminescent reporter phages (ARPs). ARPs are packaged into phage particles and are released by lysing the host cells at about 30° C.; and the phages are not formed at 37° C. After ARP enters the host, the host can produce the enzymes and substrates required for the luminescent reaction to emit luminescence.

Furthermore, genetic manipulation of Mtb is difficult in basic research. Phage carrying a highly efficient transposon has been a powerful tool for efficiently disrupting the Mtb genes and obtaining a genetically disrupted mutant strain[3]. Attempts have been made to use such phage-based transposon system to disrupt selectable marker-free auto-luminescent strains. However we found that a large part of the transposon was inserted into the vector carrying the auto-luminescent elements which inserted into its genome but not disrupted genes of the host. This introduce difficulty to the construction of the auto-luminescent Mtb transposon mutants. Therefore, it is believed that by placing the auto-luminescent element on the transposon, along with insertion into the genome of wild-type Mtb, the transposon-inserted mutants can be auto-luminescent, and the insertion sites are assured to be in the genome.

Conventional bacteriological diagnosis of Mtb have many disadvantages, such as low sensitivity, complicated operation, long duration, many influencing factors, and difficulty in standardization due to its intrinsic slow growth rate. As a result, the bacteriological diagnosis cannot fully meet the demand of clinical diagnosis. Methods of diagnosing mycobacteria/Mtb in samples and their advantages and disadvantages are shown in Table 1. Methods available for detecting clinical sensitivity of mycobacteria/Mtb to drug and their advantages and disadvantages are shown in Table 2.

TABLE 1

Methods of diagnosing mycobacteria/Mtb in sputum samples and advantages and disadvantages thereof

| Diagnostic methods | Advantages | Disadvantages | Comments |
|---|---|---|---|
| Acid-fast StainTest[4] | Rapid, economical, simple and visible. | Has a low sensitivity (>10,000 bacteria/mL, detection limit); unable to distinguish between dead and live bacteria; only mycobacteria and even other bacteria can be identified; high probability of missed diagnosis. | most widely used in diagnosing mycobacterial infection in clinical applications; a significant monitoring index for chemotherapeutic effect. |
| Lowenstein-Jenden Culture[5] | 100 bacteria/mL, detection limit. | Has a moderate sensitivity, a low positive rate, easy contamination, slow (more than 3 weeks, generally 4-8 weeks); and a large workload, and is difficult to standardize. | Gold standard of TB (tuberculosis) diagnosis, widely used in clinical applications, a significant monitoring index for chemotherapeutic effect. |
| Rapid Culture[6] | Automatic microbiological culture system, sensitive (about 10% higher than Lowenstein-Jenden Culture; at least 9 days to detect live bacteria. | Susceptible to contamination, slow (generally 5-45 days); instruments and reagents are expensive. | |
| Flow Cytometry Assay [7] | Fluorescein diacetate (FDA) can bind to live bacteria; objective, accurate, sensitive and rapid. | The flow cytometer is expensive with difficult operation, and low specificity for Mtb. | Difficult for promotion. |
| Bio-luminescence Assay[8] | Rapid and visible | Specificity and sensitivity need to be improved. | great potential. |
| PCR[9] | Rapid and simple, if no sequencing is required; and is also very sensitive. | Susceptible to contamination, and has a high false-positive rate; unable to distinguish between dead and live bacteria, and complicated sample preparation and operation. | Still not widely used over many years. |
| GenXpert[10] | Sensitive and convenient to operate, and capable of rapid diagnosis of drug resistance to RIF. | The equipments are very expensive, with a high demand for operator; unable to distinguish between dead and live bacteria. | Extremely expensive equipments (currently in international promotion). |
| Bioluminescence Quantitative PCR[11] | Sensitive. | Expensive, time consuming, and requires DNA extraction for a judgment curve; high demand for operator, and cannot distinguish between Mtb and NTM very well. | Has already been an auxiliary examination item widely used in hospitals in China, its result can work as one of the indexes for diagnosis of bacteriological negative TB; developed products include kits from DAAN GENE Inc. |
| Gene Probe Assay[12] | RNA amplification; adopting a mediated amplification | A low copy number of mRNA and is easily degraded; A high copy number of rRNA with overstability | Quality and quantity of the extracted RNA are important issues for RNA amplification method. Furthermore, |

TABLE 1-continued Methods of diagnosing mycobacteria/Mtb in sputum samples and advantages and disadvantages thereof

| Diagnostic methods | Advantages | Disadvantages | Comments |
| --- | --- | --- | --- |
| | method and hybridization protection technique; capable of rapid detection of live bacteria; requires only one tube during process to avoids cross contamination. | | RNA expression of the bacteria from RIF-treated patients may be affected. |
| Antibody-detecting Protein Chip Assay[13] | Rapid and simple. | Has a low sensitivity | Relatively weak antigenicity of Mtb and the presence of intergeneric and interspecies common antigenic determinants, as well as the inadequately illustrated correlation between humoral immunity and TB. |
| Loop-mediated Isothermal Amplification (Lamp)[14] | Sensitive, simpler than RT-PCR | Requires lysed bacteria and DNA enrichment, complicated procedure. | Developed corporations include EIKEN (China) Co., Ltd. |
| Phage amplified biologically (PhaB) assay[15] | Simple, rapid, and sensitive (about 100 CFU per reaction, close to PCR), capable of specific detection of live bacteria, and is suitable for promotion in primary hospitals. | Has a higher detection rate than bacterium culture method, unable to identify NTM; hard to be carried out, many false positive; the infection time needs to be accurately mastered; the temperature for preparing soft-agar medium must be strictly controlled; developed products include FAST plaue TB kit of BIOTEC (UK) Inc. | First reported by Wilson et al. on *Nature Medicine* in 1997; the detection takes about 18-24 hours; experimental results from multiple companies, institutes or organizations (including one of the participants Yaoju Tan) indicated considerable effect of such assay in live bacteria diagnosis, and drug sensitivity analysis, and its patents are expired. |
| Luciferase reporter phage assay[16] | Simple, rapid and specific detection of live bacteria. | The culture medium is susceptible to contamination; expensive substrate fluorescein is required to be added in, and the ability of the substrate of penetrating the cell wall is poor; the level of an another substrate ATP is greatly affected by the metabolic state of the bacteria; has low sensitivity. | First reported by Jacobs et. al on Science in 1993, few clinical trials of such method have been reported in China, and its patents are expired. |
| GFP-expressing phage assay[17, 18] | Simple, rapid, sensitive and specific. | GFP is an auto-fluorescent protein, the GFP expressing phage can identify dead, live and uncultured bacteria indistinguishably, and emit luminescence, as a result the physiological state of bacteria cannot be distinguished; difficult for detection. | Few clinical trials of such method have been reported in China. |

TABLE 2

Methods of detecting drug sensitivity of mycobacteria/Mtb and advantages and disadvantages thereof

| Diagnostic methods | Advantages | Disadvantages | Comments |
|---|---|---|---|
| Absolute concentration method | Classical and reliable. | Time consuming. | A method for drug sensitivity test which has been adopted for more than 30 years in China. |
| Proportion method | Most typical and reliable. | Time consuming. | A standard method for drug sensitivity test recommended by Resistance Surveillance Project of WHO, the method was proposed by Prof. Jacques Grosset, former president of TB research. |
| Turbidimetric resistance assay | // | Stopped of use due to its complexity. | |
| DNA chip assay | Simple, rapid and sensitive, and is suitable for mass clinical initial drug resistance screening for Mtb strains. | Requires the preparation of target gene fragment by PCR beforehand, and has complicated experimental procedure. | Remains in the stage of experimental development, and is expensive. |
| GenXpert | Rapid and simple. | Extremely expensive, and mainly detects RIF sensitive-related genes | Recent studies have indicated that such technique has not improved the cure rate of TB in developing countries |
| Bioluminescence assay (detection of ATP content in live bacteria) | Rapid (result can be obtained in 3-7 days with good reproducibility). | The ATP extraction is complicated, and the detection is expensive. | |
| Luciferase Reporter Phage Assay [16] | Simple, rapid and specific in detecting live bacteria | The culture medium is susceptible to contamination; expensive substrate fluorescein is required to be added in, and the ability of the substrate of penetrating the cell wall is poor; the level of an another substrate ATP is greatly affected by the metabolic state of the bacteria; has low sensitivity. | As mentioned above, few clinical trials of such method have been reported in China |
| Flow Cytometry Assay [7] | Fluorescein diacetate (FDA) can bind to live bacteria; such method is objective, accurate, sensitive and rapid (only takes one day at fastest speed) | The flow cytometer is expensive, with relevant techniques uneasy to master, its specificity for Mtb is low, and is susceptible to contamination of miscellaneous bacteria | Difficult for promotion |

Mycobacteriophage can be used for rapid diagnosis and detection of sensitivity of the host to a drug, such as Mtb due to its host specificity to mycobacteria. Considering the application of ARP in diagnosis and detection of drug sensitivity, the methods for phage-based detection and products related (close) to the present invention are shown in Tables 1 and 2.

The main phage-based detection methods include: Phage amplified biologically assay (PhaB assay)[15], luciferase reporter phage assay (LRP assay)[16] and GFP-expressing phage detection assay (EGFP-phage assay)[17, 18]. The PhaB assay adopts wild D29 mycobacteriophage, of which the principle is shown in FIG. 1. In this assay, D29 mycobacteriophage is used to infect live mycobacteria and kills the phages outside Mtb with a phage-killing agent, while the phages inside Mtb remain alive; and then fast growing *mycobacterium* cells (e.g. *M. smegmatis*) are introduced for a co-culture of about 18 hours for phage amplification. D29 is amplified in a large amount inside the infected bacteria, leading to dissolution of the bacteria and plaques production. Finally, the initial amount of Mtb is estimated by measuring the number of plaques. Compared to the conventional acid-fast staining method, although the phage infection requires at least 18-24 hours to identify the presence of Mtb, the optimal detection sensitivity is 100 bacteria/reaction under ideal conditions, which is close to the PCR method. Clinically, Yaoju Tan et al. have compared and analyzed 3168 sputum samples and found that the Mtb in sputum samples may be detected using PhaB assay, with the positive rate consistent with the smear method and Lowenstein-Jenden culture method[19]. It has also been reported that this method can also be used for rapid drug sensitivity test (24-72 hours), and the consistency is up to 93% as compared to the traditional plate method[20]. This method is more common in clinical verification and publications, yet it is still an alternative with few clinical applications because of complicated operation, great chance of false positives, susceptibility to contamination and sensitivity to be improved.

Figure 2:
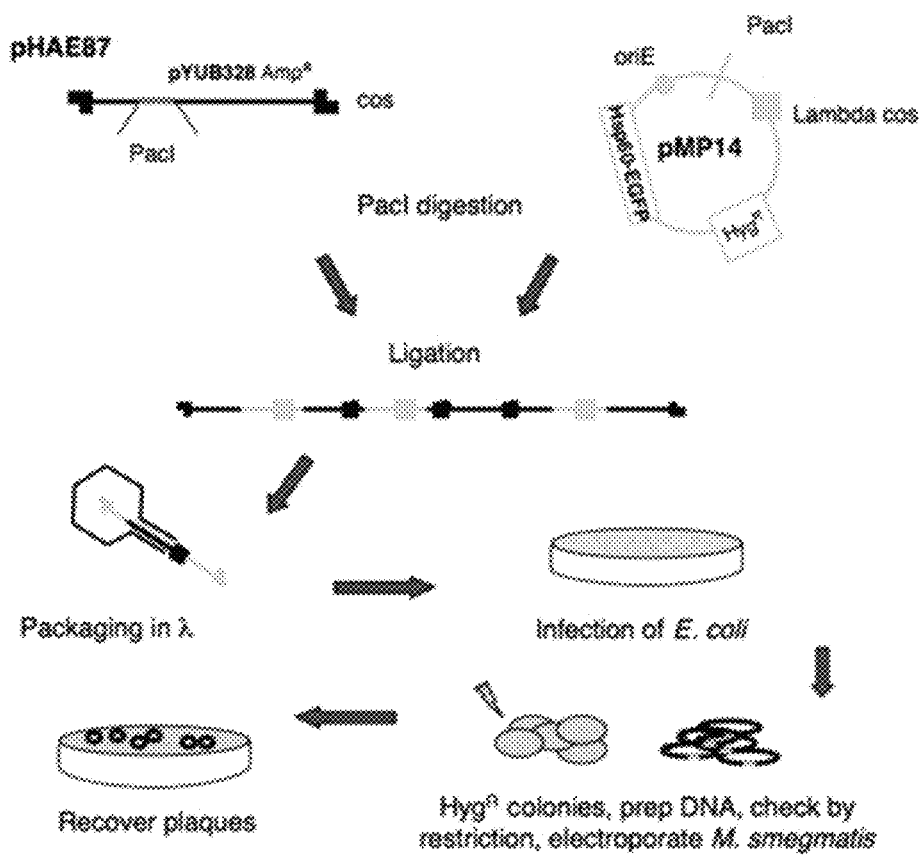

The LRP assay and EGFP-phage assay both use the constructed recombinant reporter phage to detect the presence of live phage and drug sensitivity of live bacteria (as shown in FIG. 2). The LRP assay has been published in 1993, even earlier than the PhaB assay reported in 1997. However, The LRP assay has not been developed as a product and have been reported in China and abroad in few clinical applications, owing to the addition of an expensive fluorescein substrate, the weak ability of the substrate to penetrate the cell wall of mycobacteria, unclear relationship between luminescence value and the number of live bacteria and a uncertain accuracy of detection. It was first reported in 2009 that EGFP-phage was constructed and used for rapid diagnosis and drug sensitivity test. The detection method mainly detects the EGFP protein produced after EGFP-phage's infection of live bacteria by bioluminescence microscopy or flow cytometry, while the detection sensitivity is low due to the limitations of the detection method. Moreover, operation of the method is complicated and Mtb may be easily exposed to air, causing the environment to be contaminated by Mtb. However, bioluminescence can still be detected even if formalin is used to fix and kill Mtb, thus preventing Mtb from contaminating the environment. It takes 4 hours under laboratory conditions to detect Mtb in a sample at the fastest speed. To test drug sensitivity, it takes 16 hours for rifampicin and streptomycin at the fastest speed. As for isoniazid, in order to detect the sensitivity of Mtb to INH, Mtb bacteria needs to be pretreated as follows: culturing Mtb for 24 hours followed by another 16 hours of culture. Flow cytometry is more expensive and however the results are similar. Moreover, Mtb itself has a certain background bioluminescence, which also has an impact on experimental results.

As previously mentioned, the main methods of diagnosing live Mtb and detecting sensitivity of clinical bacterial strains to the drug are based on the BD MGIT960 system for detecting the bacterial growth and the aforementioned phage-based methods.

The BD MGIT960 system is used as a main method in clinical practice. The main disadvantages of the system include: 1) slow, requiring 5-45 days for diagnosis, and another 9-12 days for sensitivity detection; 2) expensive, not only for the culture and the detection equipment, but for the culture medium and the experimental supplies; specifically, requiring a special medium and a 70-RMB (CNY) tube for detecting a single concentration of a single drug; 3) complicated operation, being difficult and time-consuming; and 4) occupying a large space for its large size.

The PhaB method has the following disadvantages: 1) complicated operation, uneasy to master: the phage infection time needs to be accurately mastered, otherwise, incomplete infection or the lysing of live cells after infection will occur, reducing the sensitivity; and difficult operational procedures are required, including preparing culture plate; 2) occupying a large space due to a large size of the device; and 3) higher cost of diagnosis and drug sensitivity test as compared to the present invention.

As for the LRP method, a related product has been developed even till its patents expired. This could be because the reaction requires an expensive fluorescein substrate with a weaker ability to penetrate the mycobacterial cell wall. Other disadvantages include unclear relationship between luminescence value and the amount of live bacteria an uncertain detection accuracy.

The EGFP-phage method has the following disadvantages: 1) flow cytometer is expensive to purchase and use; fluorescence microscope is also expensive; the fluorescence of green fluorescent protein need to be detected with the help of excitation light; fluorescence can also be observed in dead cells, thus interfering with the experimental results; and Mtb itself has a certain background fluorescence; 2) the detection sensitivity is low due to the limitations of the method and tool; 3) the operation is complicated and difficult to master compared to the present invention; and 4) the detection efficiency is low.

The aforementioned method of constructing artificial recombinant phages (FIG. 2) has serious problems, that is, when using 2 phage for in vitro packaging, the DNA packaging range is limited, and therefore it is difficult to construct large-fragment DNA into the recombinant phage by this method. For example, the Fluc and egfp genes are only about 1 kb and the auto-luminescent elements are about 6 kb, which cannot be packaged in vitro using X phage (we have tried following the same protocol, and the results have proven that such a protocol does not work).

The current recombinant mycobacteriophage is a recombinant phage recombined either with a reporter gene (such as the small reporter gene Fluc and egfp mentioned above) or a highly efficient transposon (MycoMarT7, etc.[3, 21]), yet there are currently no reports indicating that the long luxCD-ABE gene set can be inserted in a highly efficient transposon and thereby recombined into a mycobacteriophage.

In addition to the above diagnostic techniques, gene disruption is often required in the basic research of Mtb application, such as studies on gene functions, and the knock-out and disruption of virulence-related genes. Meanwhile, if the mutant strain is auto-luminescent, it will undoubtedly provide significant improvement in the efficiency of research and development. However, there is currently no such a tool.

SUMMARY OF THE PRESENT INVENTION

In order to solve the above problems, the applicant has, through extensive efforts and experimental research, succeeded in constructing artificial phasmids and a phage (ARP) capable of delivering a set of auto-luminescent elements. The phasmid constructed has the following characteristics: the auto-luminescent element carried is present on a highly efficient transposon, which can be randomly inserted into the host genome in an efficient manner, disrupting the host genes on the one hand, and enabling auto-luminescence of the host bacteria on the other hand. Therefore it can be convenient to efficiently study the function of the disrupted host gene by utilizing the feature of auto-luminescence.

An objective of the present invention is to provide a phage capable of enabling auto-luminescence of host bacteria. Meanwhile, ARP can be used to rapidly prepare auto-luminescent host bacteria (e.g. Mtb), such that such that the auto-luminescent bacteria can be convenient for drug screening, evaluation, vaccine screening and etc, as well as for in vivo studies in small animals, which in this case can be performed conveniently by detecting luminescence values after the infection of the small animals.

Another objective of the present invention is to provide a phage capable of delivering the auto-luminescent element set for diagnosis of live mycobacterium.

Yet another objective of the present invention is to provide a use of the phage in detecting a bacterium and/or sensitivity of a bacterium to a drug.

A phasmid enabling auto-luminescence of a host bacterium includes a DNA fragment including a LuxCDABE gene enabling auto-luminescence of the host bacterium.

Further, the DNA fragment includes a transposon system, a resistance gene and/or a promoter.

Further, the transposon system transposes the DNA fragment to a host genome.

Further, the transposon system is selected from Himarl mariner family or TnA family.

Further, the resistance gene is selected from at least one of hygromycin resistant gene Hyg, kanamycin resistant gene Kan, thiostrepton resistant gene Tsr and apramycin resistant gene Apr.

Further, the promoter allows for normal expression of a gene upstream of or downstream of a site in the host genome to which the DNA fragment is transposed.

Further, the promoter is selected from at least one of Mop, G13, Hsp60 and A37 promoters.

Further, the transposon system comprises a transposase gene and inverted repeat sequences. The resistance gene and the LuxCDABE gene are ligated together to form a LuxCDABE gene-resistance gene fragment. A promoter is ligated at both ends of the LuxCDABE gene-resistance gene fragment to form a promoter-LuxCDABE gene-resistance gene-promoter fragment. The promoter allows for normal expression of a gene upstream of or downstream of a site in the host genome to which the DNA fragment is transposed; and each end of the promoter-LuxCDABE gene-resistance gene-promoter fragment is ligated with each of two inverted repeat sequences in the transposon system to transpose the promoter-LuxCDABE gene-resistance gene-promoter fragment to the host genome by transposase.

Further, the DNA fragment includes a replication origin capable of replication in *Escherichia coli*, which allows the DNA fragment to replicate in a large amount in a plasmid or phasmid.

Further, the replication origin is oriE.

Further, the DNA fragment further includes a recombination site capable of homologous recombination with a phasmid backbone, which allows the DNA fragment to be ligated to the phasmid backbone.

Further, the phasmid backbone comprises a phAE159 backbone.

Further, the DNA fragment is represented by SEQ ID NO: 1.

Further, the phasmid includes a phAE159 backbone, and the DNA fragment is located between two recombination sites of the phAE159 backbone.

In the present invention, a method of preparing the phasmid includes:

digesting a phasmid backbone into a linear sequence to allow the phasmid to be recombined with a target fragment containing the LuxCDABE gene;

mixing the digested phasmid backbone with the target fragment containing the LuxCDABE gene and transforming *Escherichia coli* competent cells with the mixed digested phasmid backbone and the target fragment for recombination and amplification; and extracting the plasmid from positive recombinant *Escherichia coli* to obtain the phasmid.

Further, the method includes digesting a phasmid backbone phAE159 with restriction endonuclease PacI, and recovering a large-fragment product after digestion; mixing the recovered product with a base fragment according to SEQ ID NO: 1, and transforming *Escherichia coli* competent cells with the mixed product and the base fragment; and extracting the plasmid from a positive recombinant *Escherichia coli* to obtain the phasmid.

Further, a method of preparing the base fragment according to SEQ ID NO: 1 includes:

1) Construction of a pUCF2 Plasmid:

artificially synthesizing a F0 fragment of SEQ ID NO: 2; ligating the F0 fragment to a pUC19 vector to obtain a pUCF0 plasmid; digesting the pUCF0 plasmid with restriction endonuclease XbaI, and recovering a fragment of about 2.8 kb; ligating the fragment digested by XbaI and containing hygromycin resistant gene Hyg with the two recovered fragments to obtain a pUCF2 plasmid of about 3.9 kb;

2) Construction of a pUCF3 Plasmid:

artificially synthesizing a F1 fragment according to SEQ ID NO: 3; ligating the F0 fragment to a pUC19 vector to obtain a pUCF1 plasmid; digesting the pUCF1 plasmid with restriction endonucleases KpnI and EcoRI and recovering a fragment of about 2.7 kb; digesting the pUCF2 plasmid with restriction endonucleases KpnI and EcoRI; recovering a fragment of about 1.3 kb, and ligating the two recovered fragments to obtain a pUCF3 plasmid of about 4 kb;

3) Construction of a pUCRLlux2P Plasmid:

digesting the pUCF3 plasmid with restriction endonucleases KpnI and EcoRI, and recovering a fragment of about 3.9 kb; digesting a pluxOK plasmid with restriction endonucleases KpnI and EcoRI, and recovering a fragment of about 6.3 kb; ligating the two recovered fragments to obtain a pUCRLlux2P plasmid of about 10.2 kb;

4) Construction of a pYUBT Plasmid:

amplifying a transposase trans gene sequence from a MycoMarT7 phage, adding a NcoI restriction site to a 5' end of the trans gene, adding a SpeI restriction site to a 3' end of the trans gene, and digesting the amplified product with NcoI and SpeI and recovering a fragment of about 1 kb; digesting a pYUB854 plasmid with restriction endonucleases NcoI and SpeI, and recovering a fragment of about 3.8 kb; ligating the two recovered fragments to obtain a pYUBT plasmid;

5) Construction of a pYUOK Plasmid:

digesting a pUCRLlux2P plasmid with restriction endonucleases NcoI and and recovering a fragment of about 7.6 kb; digesting the pYUBT plasmid with restriction endonucleases NcoI and XbaI, and recovering a fragment of about 2.9 kb; ligating the two recovered fragments to obtain a pYUOK plasmid of about 10.5 kb;

6) Construction of a p159LART Plasmid:

synthesizing a base fragment according to SEQ ID NO: 4, ligating the base fragment to a pUC19 vector to obtain a p159LR plasmid, digesting the p159LR plasmid with NheI and recovering a fragment; amplifying a Apr gene fragment with a NheI restriction site at both ends, digesting the fragment with restriction endonuclease NheI and recovering a fragment; ligating the two recovered fragments to obtain a p159LART plasmid of about 4.8 kb;

7) Construction of a pYUOKLART Plasmid:
digesting the pYUOK plasmid with restriction endonuclease PacI, and recovering a fragment of about 10.5 kb; digesting the p159LART plasmid with restriction endonuclease PacI, recovering a fragment of about 2 kb, and ligating the two recovered fragments to obtain a pYUOKLART plasmid of about 12.5 kb; and 8) Production of a Base Fragment According to SEQ ID NO: 1
digesting the pYUOKLART plasmid with restriction endonuclease recovering a large-fragment product after digestion to obtain the base fragment according to SEQ ID NO: 1.

A phage capable of delivering an auto-luminescent element includes the phasmid of the present application.

A use of the phage in detecting a host bacterium and/or drug sensitivity of a host bacterium is provided.

Further, the host bacterium is *Mycobacterium*.

Further, the *mycobacterium* includes Mtb, *Mycobacterium smegmatis, Mycobacterium marinum* and *Mycobacterium* Bacille Calmette-Guerin (BCG).

A method of detecting a host bacterium with the phage includes the following steps:

1) adding a phage-containing liquid to a sample to be tested;
2) culturing the sample at 36.5-42° C. for 35 minutes or more, and detecting bioluminescence using a luminometer;
3) if there is a significant bioluminescence compared to a negative control group without ARP, indicating the sample contains a large amount of live mycobacteria; if the bioluminescence intensity is lower than 120% of the bioluminescence intensity of the negative control, adding a phage-killing reagent SK to kill the phage whose genome has not entered the *mycobacterium*; wherein the SK reagent is selected from at least one of ammonium sulfate, ferrous sulfate, ammonia sulfate and ammonium ferrous sulfate;
4) adding a neutralizing agent SN to neutralize the excess SK reagent, adding an indicator bacterium, and culturing the sample at 20-32° C. for 12 hours or more; wherein the neutralizing agent SN is selected from at least one of MgSO4, potassium dichromate, $CaCl_2$ and $MnCl_2$; and
5) detecting luminescence of the sample added with the indicator bacterium with a luminometer; wherein the luminescence indicates the presence of live mycobacteria in the sample; non-luminescence indicates the absence of live mycobacteria in the sample.

Further, the indicator bacterium is a host of the phage, and the phage proliferates and lyses cells in the host.

A method of detecting sensitivity of a host bacterium to a drug with the phage includes the following steps:

1) mixing the phage with the host bacterium, and adding a certain concentration of a drug to be tested;
2) culturing the mixed phage and the host bacterium at 36.5-42° C. for at least 2 hours, and detecting luminescence using a luminometer; and
3) if there is significant difference between the luminescence of the tested sample and the luminescence of a sample with no drug, indicating the host bacteria is sensitive to the drug of the concentration; if there is no significant difference, indicating the host bacteria is resistant to the drug at the concentration.

The present invention has the following beneficial effects:
1) The present invention relates to the concepts of synthetic biology, where a novel artificial mycobacteriophage (ARP) was successfully constructed by utilizing synthetic DNA, and approaches including genetic engineering and molecular biology. ARP is a temperature sensitive phage. It can lyse the host under a temperature below 30° C., while it cannot lyse the host at 37-42° C. By delivering auto-luminescent gene elements to the host, ARP can make its host *mycobacterium* express its corresponding proteins (enzymes). These enzymes can utilize the metabolites of live host bacteria to circulate the generation of substrates required for the luminescence reaction, as well as the enzymes required for the reaction. Therefore, the live host bacteria may be luminescent without addition of any substrate. The auto-luminescent element carried by the ARP of the present invention is present on a highly efficient transposon, along with which the element can be randomly inserted into the host genome in an efficient manner, disrupting the host genes on the one hand, and enabling the auto-luminescence of the host bacteria with disrupted genes on the other hand. It is important that the ARP can rapidly diagnose live host bacteria in a sample and rapidly test the drug sensitivity of a host strain. Such diagnosis and detection are about 8-40 days faster than the most popular BD MGIT 960 system on the market, and are simpler, more intuitive and more economical. The ARP has certain preference for its host in mycobacteria, and Mtb is one of the most important host bacteria.

2) The phage constructed by the present invention can transform a *mycobacterium* and enable the auto-luminescence of the transformed *mycobacterium* after incubation at a temperature. The *mycobacterium* includes, but is not limited to *Mycobacterium smegmatis*, Mtb and BCG.

3) According to the characteristics of the host bacterium, the present invention can prepare a host bacterium-specific phage capable of delivering the auto-luminescent elements. The auto-luminescent *mycobacterium* is obtained after the phage is transduced into the *mycobacterium*. Since the mycobacteriophage has host specificity (specific to *mycobacterium*), the phage can be used for rapid detection of a live *mycobacterium*.

4) The present invention provides a p159OK phasmid for constructing the phasmid of the auto-luminescent bacterium. The phasmid includes a phAE159 phage backbone, a mycobacterial strong promoter (Hsp60); a gene required for luminescence (LuxCDABE); a hygromycin resistant gene (Hyg); a transposase gene (Trans); inverted repeat sequences IR-L and IR-R; and Mop and G13 promoters. The luminescent *mycobacterium*, obtained by the transformation of the host with the phasmid or the phage produced from the phasmid, is an auto-luminescent *mycobacterium*. The phasmid or the phage is convenient for detection with high accuracy, and can be used for detection of sensitivity of a *mycobacterium* to a drug.

5) The present invention has skipped a packaging process of X phage. Early studies by the applicant adopted the packaging process of X phage, yet the applicant failed to obtain the p159OK phasmid despite of repeated a large amount of experimental studies, and this cannot succeed in theory. Since such packaging process of X phage was skipped, the present invention was not limited to the size of the X phage packaging, and achieved good experimental results. The p159OK phasmid was successfully constructed with a size capable of more than 57 kb, while the size of the largest vector that can be obtained by the existing X phage packaging does not exceed 52 kb.

6) Even if the auto-luminescent elements are not integrated into the genome, the host bacteria can still be auto-luminescent. The ARP obtained by the invention may efficiently introduce the carried auto-luminescent element into Mtb and BCG, to allow the live Mtb to be luminescent (dead bacteria are not luminescent), thereby rapidly diagnosing the live host bacteria in a sample and quickly testing the sensitivity of the host bacteria to a drug. In order to increase the sensitivity of the diagnosis, a bacteriophage-killing agent (neutralizer) and an indicator bacterium (*Mycobacterium smegmatis* $MC^2$ 155; Msm) amplifying the signal are used. The reaction is carried out in the same tube that is inexpensive, with a strong luminescence signal detectable over a long period of time.

7) The artificial phage provided by the present invention can be used in the following applications: i) efficient preparation of an auto-luminescent *mycobacterium* transposon mutant strain, which facilitates the studies of gene functions; ii) simple, economical and rapid diagnosis of live Mtb in a sample, with the specificity of the phage used to assist in the identification of bacterial species; and iii) simple, economical and rapid drug susceptibility testing (DST).

8) By using the auto-luminescent phage obtained by transforming the host bacteria with the phasmid of the present invention, dead and live bacteria can be distinguished by detecting luminescence, which is suitable for various experiments or tests.

9) The auto-luminescent *mycobacterium* prepared through the transduction of ARP of the present invention can be used for in vitro drug activity test, and does not require any substrate. The lights from the same sample can be continuously with a high sensitivity and a high reproducibility.

BRIEF DESCRIPTION OF THE DRAWINGS

FIG. 1 is a schematic diagram of the Phage Amplified Biologically method (PhaB method) (BIOTEC, U.K); wherein the infection time needs to be accurately controlled, otherwise the cells may be incompletely infected or lysed after infection, resulting in a reduced sensitivity; and the shortest time to complete infection is 18-24 hours.

FIG. 2 is a schematic diagram of the construction of recombinant reporter phage; where the construction of EGFP-phage is shown for exemplary illustration: the reporter gene is an enhanced green fluorescent protein gene (egfp)[17,18]; the reporter gene for the recombinant reporter phage of the LRP method is the firefly luciferase gene (Fluc); and the difference between the two methods is reporter genes.

FIG. 3 is a flow chart showing the construction of a pUCRLlux2P plasmid.

FIG. 4 is a flow chart showing the construction of a pYUOK plasmid.

FIG. 5 is a flow chart showing the construction of a pYUOKLART plasmid.

FIG. 6 is a flow chart showing the construction of a p159OK phasmid.

FIG. 7 is a flow chart of a rapid detection of a host *mycobacterium* in a sample with ARP phages.

FIG. 8 shows the bioluminescence intensity of Mtb strain under laboratory conditions which is detected with ARP of the present invention at different time of culture.

FIG. 9 shows the results of clinical samples which are detected with the ARPs of the present invention, where the horizontal line shows the critical value for distinguishing between a negative sample and a positive sample (RLU=80, i.e., the bioluminescence intensity is 120% of that of a negative control); Con is a negative sputum smear as a control; and P1-P9 are positive sputum smears.

FIG. 10 shows the results of samples containing Mtb of different titers which are detected with the ARPs of the present invention; Con is a negative control and does not contain Mtb; "Undiluted" refers to an undiluted sample; $10^{-n}$ refers to a dilution of 10 to the power of n, and when diluted to $10^{-8}$, the number of Mtb in each sample does not exceed 10; the horizontal line shows the critical value for distinguishing between a negative sample and a positive sample (i.e., the bioluminescence intensity is 120% of that of the negative control); and the "19 h" and "24 h" are the time of culture at 30° C. after an indicator bacterium is added.

FIG. 11 is a schematic diagram of a rapid detection of sensitivity of a host *mycobacterium* to a drug with the ARPs of the present invention.

FIG. 12 shows the results of sensitivity of Mtb to a drug which is detected with the ARPs of the present invention, where the "Con" is a DMSO control without any drugs, rifampicin (RIF, 2 μg/mL), isoniazid (INH, 1 μg/mL), ethambutol (EMB, 5 μg/mL), linezolid (LZD, 1 μg/mL), oxazolidinone (PNU, 0.5 μg/mL); "n.s." represents that no statistical difference was found between the EMB group and the control ($p>0.05$); "*" represents that statistical difference was found between a test group and the control ($p<0.05$).

FIG. 13 is a schematic diagram of detection of live mycobacteria in samples and sensitivity of the mycobacteria to rifampicin (RIF), where S1-S3 are sample groups, and C1-C3 are control groups.

DETAILED DESCRIPTION OF THE PRESENT INVENTION

A phasmid enabling auto-luminescence of a host bacterium includes a DNA fragment enabling auto-luminescence of the host bacterium; and the DNA fragment includes a LuxCDABE gene cluster for luminescence.

Preferably, the DNA fragment further includes a transposon system, a resistance gene and/or a promoter.

Preferably, the transposon system transposes the DNA fragment to a host genome.

Preferably, the transposon system is selected from Himarl mariner family or TnA family.

Preferably, the resistance gene is selected from at least one of hygromycin resistant gene Hyg, kanamycin resistant gene Kan, thiostrepton resistant gene Tsr and apramycin resistant gene Apr.

Preferably, the promoter allows for normal expression of a gene upstream of or downstream of a site in the host genome to which the DNA fragment is transposed.

Preferably, the promoter is selected from at least one of Mop, G13, Hsp60 and A37 promoters.

Preferably, the transposon system includes a transposase gene and inverted repeat sequences. The resistance gene and the LuxCDABE gene are ligated together to form a LuxCDABE gene-resistance gene fragment. A promoter is ligated at both ends of the LuxCDABE gene-resistance gene fragment to form a promoter-LuxCDABE gene-resistance gene-promoter fragment. The promoter allows for normal expression of a gene upstream of or downstream of a site in the host genome to which the DNA fragment is transposed.

Each end of the promoter-LuxCDABE gene-resistance gene-promoter fragment is ligated with each of two inverted repeat sequences in the transposon system to transpose the promoter-LuxCDABE gene-resistance gene-promoter fragment to the host genome by transposase.

Preferably, the DNA fragment capable of making a host bacterium auto-luminescent further includes a replication origin capable of replication in *Escherichia coli*, which allows the DNA fragment to replicate in a large amount in a plasmid or phasmid.

Preferably, the replication origin is oriE.

Preferably, the DNA fragment further includes a recombination site capable of homologous recombination with a phasmid backbone, which allows the DNA fragment to be ligated to the phasmid backbone.

Preferably, the phasmid backbone comprises a phAE159 backbone.

Preferably, the DNA fragment is represented by SEQ ID NO: 1.

Preferably, the phasmid further includes a phAE159 backbone, and the DNA fragment is located between two recombination sites of the phAE159 backbone.

A method of preparing the phasmid enabling auto-luminescence of a host bacterium includes:

digesting a phasmid backbone into a linear sequence to allow the phasmid to be recombined with a target fragment containing the LuxCDABE genes;

mixing the digested phasmid backbone with the target fragment containing the LuxCDABE genes and transforming *Escherichia coli* competent cells with the mixed digested phasmid backbone and the target fragment for recombination and amplification; and extracting the plasmid from positive recombinant *Escherichia coli* to obtain the phasmid.

Preferably, the method includes:

digesting a phasmid backbone phAE159 with restriction endonuclease PacI, and recovering a large-fragment product after digestion;

mixing the recovered product with a base fragment according to SEQ ID NO: 1, and transforming *Escherichia coli* competent cells with the mixed product and the base fragment; and extracting the plasmid from a positive recombinant *Escherichia coli* to obtain the phasmid.

Preferably, a method of preparing the base fragment according to SEQ ID NO: 1 includes the following steps:

1) Construction of a pUCF2 Plasmid artificially synthesizing a F0 fragment of SEQ ID NO: 2; ligating the F0 fragment to a pUC19 vector to obtain a pUCF0 plasmid; digesting the pUCF0 plasmid with restriction endonuclease XbaI, and recovering a fragment of about 2.8 kb; ligating the fragment digested by XbaI and containing hygromycin resistant gene Hyg with the two recovered fragments to obtain a pUCF2 plasmid of about 3.9 kb;

2) Construction of a pUCF3 Plasmid artificially synthesizing a F1 fragment according to SEQ 1D NO: 3; ligating the F0 fragment to a pUC19 vector to obtain a pUCF1 plasmid; digesting the pUCF1 plasmid with restriction endonucleases KpnI and EcoRI and recovering a fragment of about 2.7 kb; digesting the pUCF2 plasmid with restriction endonucleases KpnI and EcoRI recovering a fragment of about 1.3 kb, and ligating the two recovered fragments to obtain a pUCF3 plasmid of about 4 kb;

3) Construction of a pUCRLlux2P Plasmid digesting the pUCF3 plasmid with restriction endonucleases KpnI and EcoRI, and recovering a fragment of about 3.9 kb; digesting a pluxOK plasmid with restriction endonucleases KpnI and EcoRI, and recovering a fragment of about 6.3 kb; ligating the two recovered fragments to obtain a pUCRLlux2P plasmid of about 10.2 kb;

4) Construction of a pYUBT Plasmid amplifying a transposase trans gene sequence from a MycoMarT7 phage, adding a NcoI restriction site to a 5' end of the trans gene, adding a SpeI restriction site to a 3' end of the trans gene, and digesting the amplified product with NcoI and SpeI and recovering a fragment of about 1 kb; digesting a pYUB854 plasmid with restriction endonucleases NcoI and SpeI, and recovering a fragment of about 3.8 kb; ligating the two recovered fragments to obtain a pYUBT plasmid;

5) Construction of a pYUOK Plasmid digesting a pUCRLlux2P plasmid with restriction endonucleases NcoI and SpeI, and recovering a fragment of about 7.6 kb; digesting the pYUBT plasmid with restriction endonucleases NcoI and XbaI, and recovering a fragment of about 2.9 kb; ligating the two recovered fragments to obtain a pYUOK plasmid of about 10.5 kb;

6) Construction of a p159LART Plasmid synthesizing a base fragment according to SEQ ID NO: 4, ligating the base fragment to a pUC19 vector to obtain a p159LR plasmid, digesting the p159LR plasmid with NheI and recovering a fragment; amplifying a Apr gene fragment with a NheI restriction site at both ends, digesting the fragment with restriction endonuclease NheI and recovering a fragment; ligating the two recovered fragments to obtain a p159LART plasmid of about 4.8 kb;

7) Construction of a pYUOKLART Plasmid digesting the pYUOK plasmid with restriction endonuclease PacI, and recovering a fragment of about 10.5 kb; digesting the p159LART plasmid with restriction endonuclease PacI, recovering a fragment of about 2 kb, and ligating the two recovered fragments to obtain a pYUOKLART plasmid of about 12.5 kb; and 8) production of a base fragment according to SEQ ID NO: 1 digesting the pYUOKLART plasmid with restriction endonuclease SmaI, recovering a large-fragment product after digestion to obtain the base fragment according to SEQ ID NO: 1.

A phage capable of delivering an auto-luminescent element includes any one of the aforesaid phasmid.

A use of the phage in detecting a host bacterium and/or drug sensitivity of a host bacterium is provided.

Preferably, the host bacterium is *mycobacterium*.

Preferably, the *mycobacterium* includes *Mycobacterium smegmatis*, Mtb, *Mycobacterium marinum* and BCG.

A method of detecting a host bacterium with the aforesaid phage includes the following steps:

1) adding a phage-containing liquid to a sample to be tested;

2) culturing the sample at 36.5-42° C. for 35 minutes or more, and detecting luminescence using a luminometer;

3) if there is a significant bioluminescence compared to a negative control group without ARP, indicating the sample contains a large amount of live mycobacteria; if the bioluminescence intensity is lower than 120% of the bioluminescence intensity of the negative control, adding a phage-killing reagent SK to kill the phage whose genome has not entered the *mycobacterium*; wherein the SK reagent is selected from at least one of ammonium sulfate, ferrous sulfate, ammonia sulfate and ammonium ferrous sulfate;

4) adding a neutralizing agent SN to neutralize the excess SK reagent, adding an indicator bacterium, and culturing the sample at 20-32° C. for 12 hours or more; wherein the neutralizing agent SN is selected from at least one of $MgSO_4$, potassium dichromate, $CaCl_2$ and $MnCl_2$; and 5) detecting luminescence of the sample added with the indicator bacterium with a luminometer; wherein the luminescence indicates the presence of live *mycobacterium* in the sample; non-luminescence indicates the absence of live *mycobacterium* in the sample.

Preferably, the indicator bacterium is a host of the phage, and the phage proliferates and lyses cells in the host.

Preferably, a culture temperature in step 2) is 36.5-37.5° C.

Preferably, a culture temperature in step 4) is 29-31° C.

A method of detecting the drug sensitivity of a host bacterium with the phage, wherein the method includes the following steps:

1) mixing the phage with the host bacterium, and adding a certain concentration of a drug to be tested;

2) culturing the mixed phage and the host bacterium at 36.5-42° C. for at least 2 hours, and detecting luminescence using a luminometer; and 3) if there is significant difference between the luminescence of the tested sample and the luminescence of a sample with no drug, indicating the host bacteria is sensitive to the drug of the concentration; if there is no significant difference, indicating the host bacteria is resistant to the drug at the concentration.

The present invention will be further described below in conjunction with specific embodiments, but is not limited thereto.

In the embodiments as will described blow, the experimental techniques of molecular biology include PCR amplification, plasmid extraction, plasmid transformation, DNA fragment ligation, restriction enzyme digestion, gel electrophoresis, etc., each of which follows a conventional protocol. See Sambrook J, Russell D W, Janssen K, Argentine J. Molecular Cloning: A Laboratory Manual (Third Edition) (Translated by Huang Peitang et al., Beijing: Science Press, 2002).

DNA polymerase, dNTP and relevant reagents for PCR reaction were purchased from Beijing TransGene Biotech Co., Ltd. *E. coli* competent cells DH5α were purchased from Guangzhou Dongsheng Biotech Co., Ltd.; product number: C1042. DNA ligation reactions were performed using Takara Biotech's T4DNA Ligation Kit; product model: D6020A. Plasmid Mini Kit (P1001), Large Plasmid Extraction Kit (P1151-02), Gel DNA Recovery Kit (D2111) and PCR Product Recovery Kit (D2120/D2121) were purchased from Guangzhou Megan Biotech Company. Restriction enzymes were purchased from Takara Biotech Co., Ltd. Ampicillin and apramycin antibiotics were purchased from Guangzhou Whiga Biotech Co., Ltd. Hygromycin B was purchased from Roche Company.

Example 1 Construction of p159OK Phasmid

Referring to FIGS. 3-6, a p159OK phasmid includes a phAE159 phage backbone; a mycobacterial strong promoter (Hsp60); an enzyme gene for luminescence (LuxCDABE); a hygromycin resistant gene (Hyg); a transposase gene (trans); inverted repeat sequences IR-L and IR-R; and Mop and G13 promoters. Functions of these elements are described below.

Hsp60: a strong mycobacterial promoter that promotes strong expression of subsequent genes.

LuxCDABE: an enzyme gene for luminescence, the expression of which allows for auto-luminescence of the host bacteria (see Halkila K, Maksimow M, Karp M, Virta M (2002) Reporter genes lucFF, luxCDABE, gfp, and dsred have different characteristics in whole-cell bacterial sensors. *Analytical biochemistry* 301: 235-242).

Hygromycin resistant gene (Hyg): a selection marker for the screening for the desired strain. Upon expression of the hygromycin resistant gene (Hyg) in *mycobacterium* and *E. coli*, the host becomes resistant to hygromycin, that is, may grow in a medium containing hygromycin antibiotics. Hyg is a typical drug for resistance screening with a Hyg concentration of 50 μg/mL for *mycobacterium* and a Hyg concentration 200 μg/mL for *E. coli*.

Transposase gene (trans): a gene encoding an enzyme that performs transposition.

Inverted repeat sequences (IR-L and IR-R): located at both ends of the transposon as its components.

Promoters (Mop and G13): mainly used for ensuring the normal expression of a gene upstream of or downstream of a site in the host genome to which the DNA fragment is transposed.

Specifically, processes for construction of plasmid are as follows.

1. Construction of pUCF2 Plasmid

Figure 3:
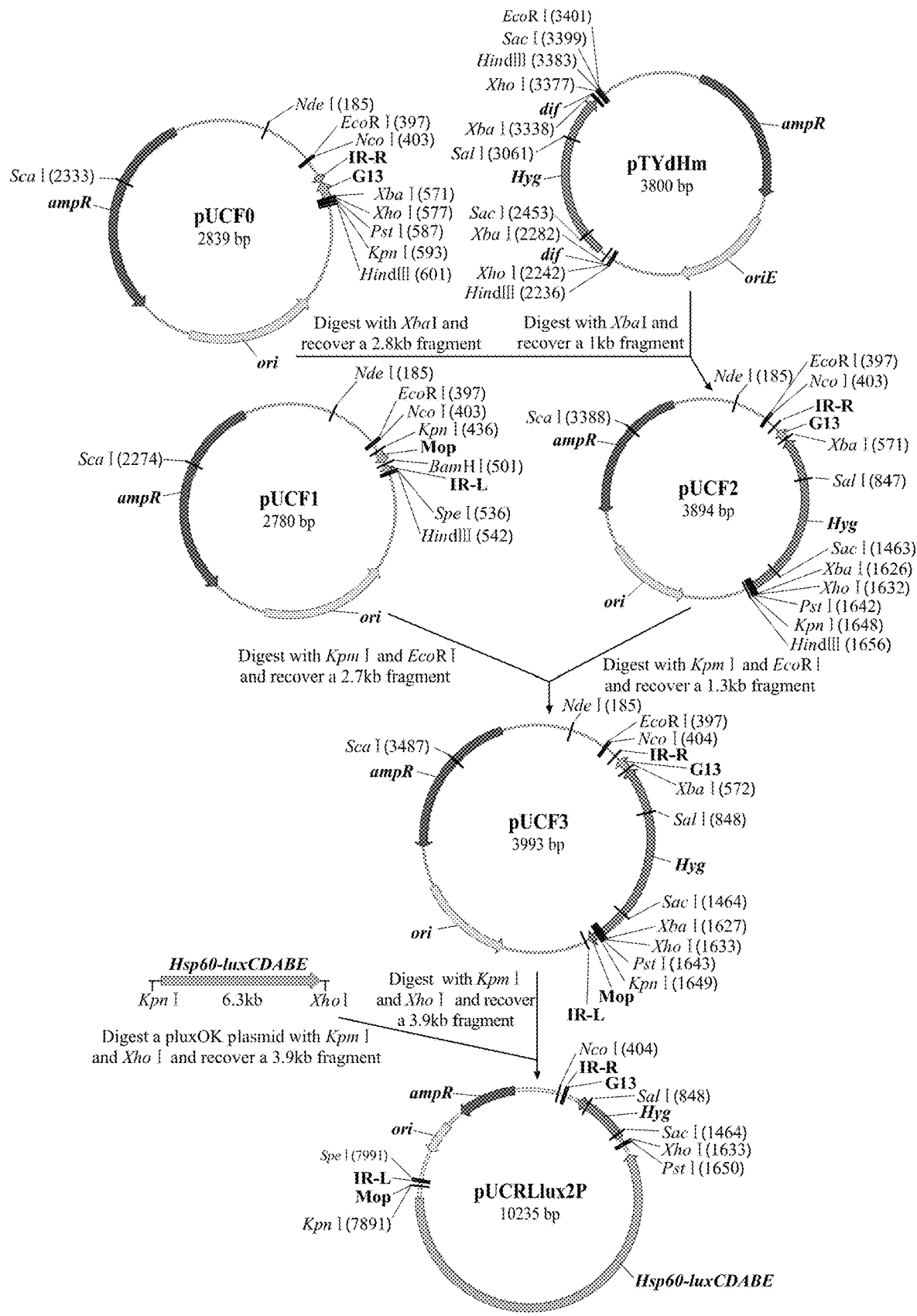

A starting plasmid pUCF0 was obtained by ligating a synthetic F0 fragment (shown as SEQ ID NO: 2; Shanghai Generay Biotech Co., Ltd) with a pUC19 vector (FIG. 3 shows a map where the F0 fragment includes a G13 promoter, an inverted repeat sequence IR-R, etc.). The pUCF0 plasmid was digested with restriction endonuclease XbaI, and a fragment of about 2.8 kb was recovered with a gel DNA recovery kit. A pTYdHm plasmid was constructed by this experiment (the map is shown in FIG. 3, and the specific method can be found in Piuri, M., W.R.J.J., and, G.F.H. Fluoromycobacteriophages for Rapid, Specific, and Sensitive Antibiotic Susceptibility Testing of *Mycobacterium tuberculosis*. *PLoS One*. 2009, 4, e487). The pTYdHm plasmid was digested with restriction endonuclease XbaI, and a fragment of about 1 kb containing Hyg was recovered. The two recovered fragments were ligated to obtain a pUCF2 plasmid of about 3.9 kb, and *E. coli* competent cells DH5c were transformed with the pUCF2 plasmid. Positive clones were screened using a LB solid plate with resistance to hygromycin. A monoclone was picked and cultured in a LB liquid medium. Then the plasmid was extracted. Direction of Hyg insertion was identified using restriction endonucleasse SalI and PstI. Two fragments of 800 bp and 3 kb can be digested from the pUCF2 plasmid which was correctly constructed.

2. Construction of pUCF3 Plasmid

A starting plasmid pUCF1 was obtained by ligating a synthetic F1 fragment (shown as SEQ ID NO: 3; Shanghai Generay Biotech Co., Ltd) with the pUC19 vector (FIG. 3 shows a map where the F1 fragment includes a Mop promoter, an inverted repeat sequence IR-L, etc.). The pUCF1 plasmid was digested with restriction endonuclease KpnI and restriction endonuclease EcoRI, and a fragment of about 2.7 kb was recovered with a gel DNA recovery kit. The pUCF2 plasmid was digested with restriction endonuclease KpnI and EcoRI, and a fragment of about 1.3 kb was recovered with a gel DNA recovery kit. The two fragments were ligated to obtain a pUCF3 plasmid of about 4 kb, and the *E. coli* competent cells DH5α were transformed with the pUCF3 plasmid. Positive clones were screened using the LB solid plate with resistance to hygromycin. A monoclone was picked and cultured in the LB liquid medium. Then the plasmid was extracted and then identified through an enzyme digestion. The pUCF3 plasmid which was correctly constructed was used for the next step.

3. Construction of pUCRLlux2P Plasmid

As shown in FIG. 3, the pUCF3 plasmid was digested with restriction endonucleases KpnI and XhoI, and a fragment of about 3.9 kb was recovered. A pluxOK plasmid (presented by Prof. Eric Nuermberger of Johns Hopkins University, US, and the specific method can be found in Forti F, Mauri V, Deho G, Ghisotti D. Isolation of conditional expression mutants in *Mycobacterium tuberculosis* by transposon mutagenesis. *Tuberculosis*. 2011; 91(6): 569-

578.) was digested with restriction endonucleases KpnI and XhoI, and a functional fragment KpnI-Hsp60-luxCDABE-XhoI of about 6.3 kb was recovered. The two recovered fragments were ligated to obtain a pUCRLlux2P plasmid of about 10.2 kb, and the *E. coli* competent cells DH5α were transformed with the pUCRLlux2P plasmid. Positive clones were screened using the LB solid plate with resistance to hygromycin. A monoclone was picked and cultured in the LB liquid medium. Then the plasmid was extracted and then identified through an enzyme digestion. The pUCRLlux2P plasmid which was correctly constructed was used for the next step.

4. Construction of pYUBT Plasmid

1) Primers ZZf (shown as SEQ ID NO: 5) and ZZr (shown as SEQ ID NO: 6) were employed to amplify a trans gene sequence (shown as SEQ ID NO: 9) from a MycoMarT7 phage. During the amplification, a NcoI restriction site and a SpeI restriction site were introduced to 5' end and 3' end of the trans gene, respectively. The amplified product was digested with NcoI and SpeI overnight and then the digested product was recovered.

Figure 4:
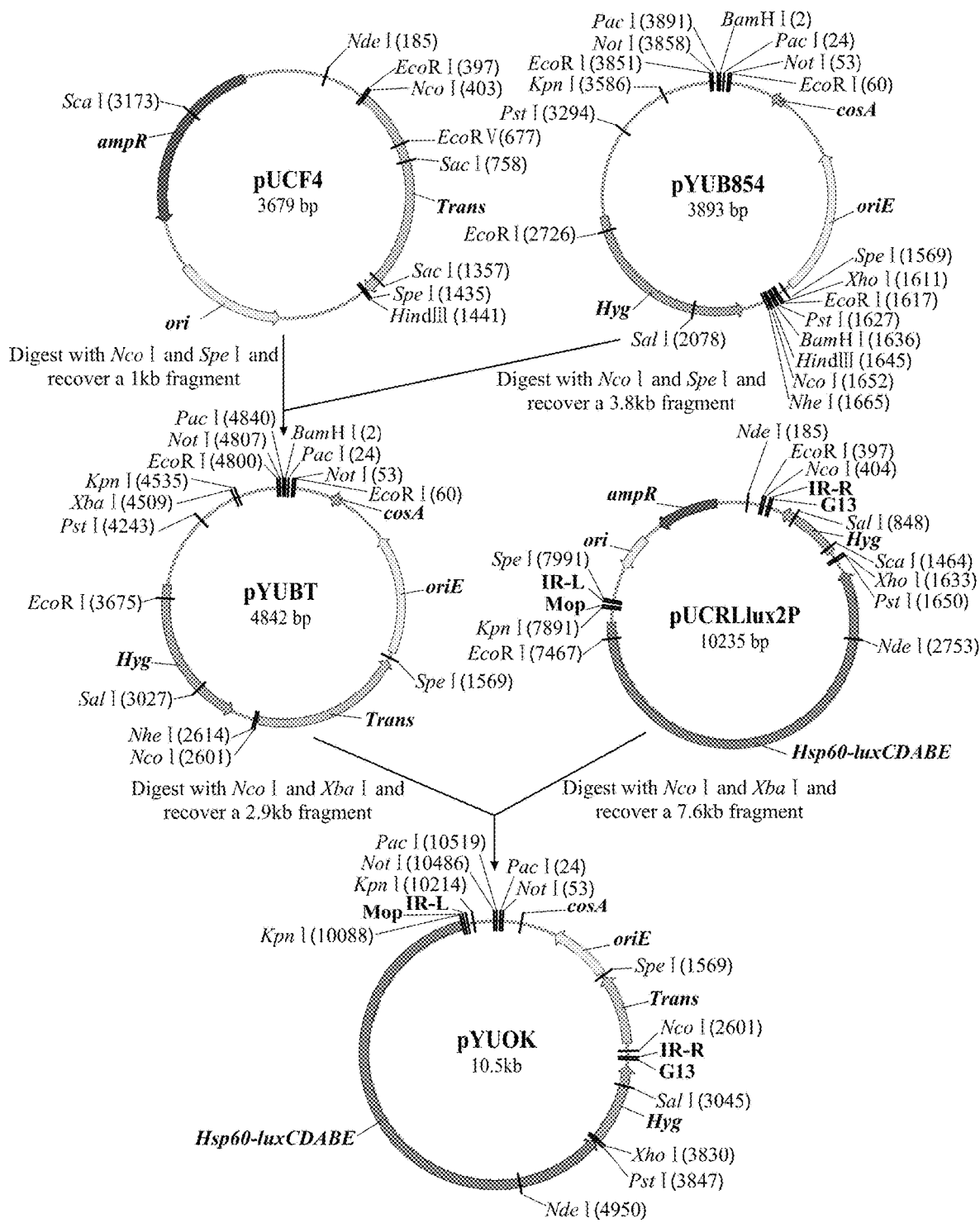

2) The pUCF2 plasmid was digested with restriction endonucleases NcoI and SpeI, and a fragment of about 2.7 kb was recovered. The two recovered fragments were ligated to obtain a pUCF4 plasmid (the map is shown in FIG. 4) of 3.7 kb. Then the pUCF4 plasmid was sequenced.

3) The pUCF4 plasmid which was correctly sequenced through trans gene was digested with restriction endonucleases NcoI and SpeI and a fragment of about 1 kb was recovered (shown in FIG. 4).

4) A pYUB854 plasmid was digested with restriction endonucleases NcoI and Spa and a fragment of about 3.8 kb was recovered (shown in FIG. 4).

5) The two fragments obtained in steps 3) and 4) were ligated to obtain a pYUBT plasmid of about 4.8 kb (shown in FIG. 4). The *E. coli* competent cells DH5u were transformed with the pYUBT plasmid. Positive clones were screened using the LB solid plate with resistance to hygromycin. A monoclone was picked and cultured in the LB liquid medium. Then the plasmid was extracted and then identified through an enzyme digestion. The pYUBT plasmid which was correctly constructed was used for the next step.

5. Construction of pYUOK Plasmid

The pUCRLlux2P plasmid was digested with restriction endonucleases NcoI and SpeI, and a fragment of about 7.6 kb was recovered. The pYUBT plasmid was digested with restriction endonucleases NcoI and XbaI, and a fragment of about 2.9 kb was recovered. Restriction endonucleases XbaI and SpeI are isocaudamers. The two fragments were ligated to obtain a pYUOK plasmid of about 10.5 kb. The *E. coli* competent cells DH5α were transformed with the pYUOK plasmid. Positive clones were screened using the LB solid plate with resistance to hygromycin. A monoclone was picked and cultured in the LB liquid medium. Then the plasmid was extracted to be identified through an enzyme digestion. The pYUOK plasmid which was correctly constructed was used for the next step.

6. Construction of p159LART Plasmid

Figure 5:
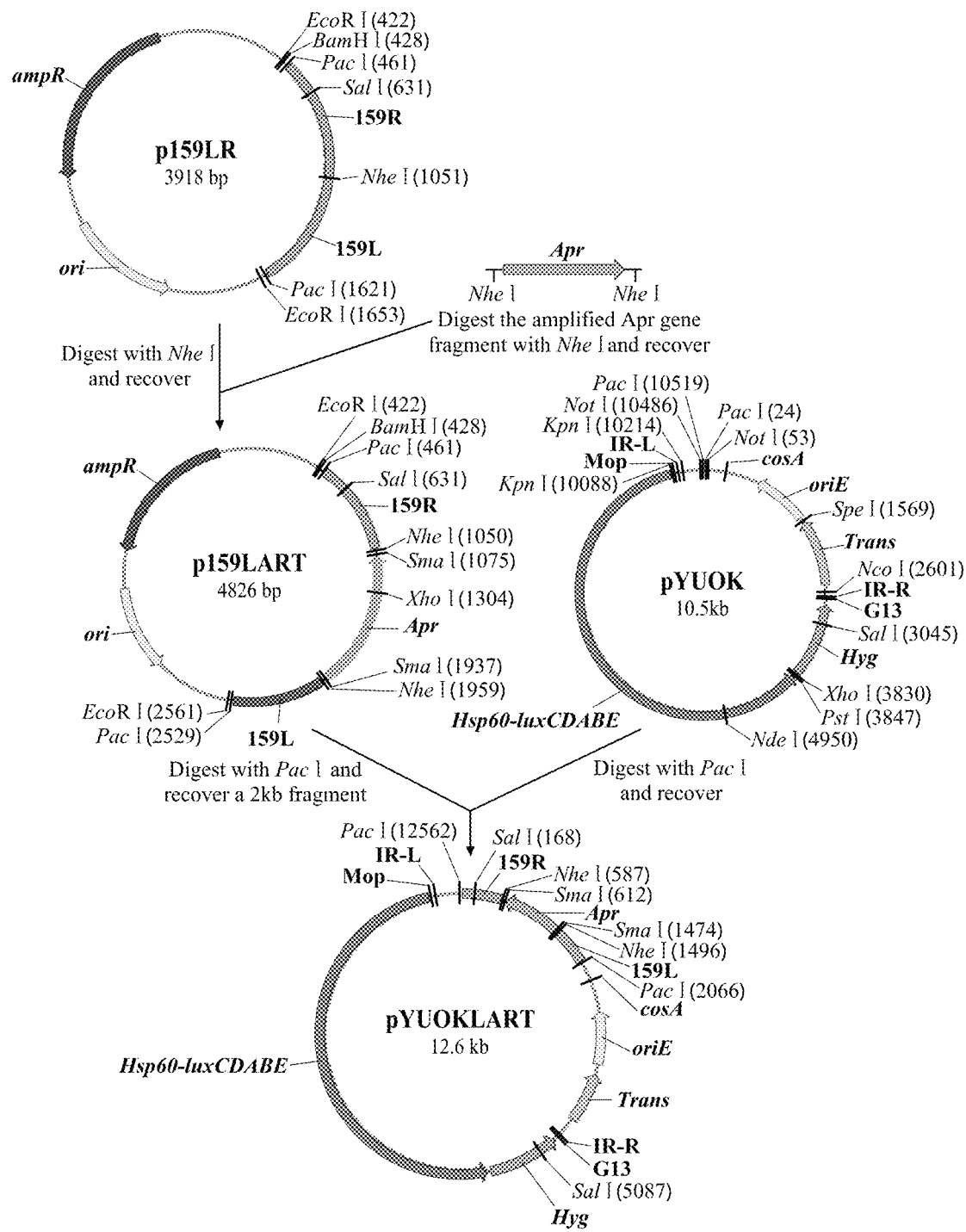

A base fragment (shown as SEQ ID NO: 4) containing two homologous recombination fragments 159L and 159R of a phAE159 plasmid was synthesized. The base fragment was ligated with a pUC19 vector to obtain a p159LR plasmid (the map is shown in FIG. 5). The p159LR plasmid was digested with restriction endonuclease NheI and the digested product was recovered. Primers AprF (SEQ ID NO: 7) and AprR (SEQ ID NO: 8) were used to amplify a Apr gene fragment from a pMH94A plasmid (prepared by our laboratory). NheI restriction sites were added to both ends of the Apr gene during the amplification. PCR product was recovered and then digested with restriction endonuclease NheI overnight. The digested product was directly recovered with a PCR product recovery kit. The two fragments were ligated to obtain a p159LART plasmid (shown in FIG. 5) of about 4.8 kb. The *E. coli* competent cells DH5α were transformed with the p159LART plasmid. Positive clones were screened using the LB solid plate with resistance to apramycin. A monoclone was picked and cultured in the LB liquid medium. Then the plasmid was extracted to be identified through an enzyme digestion. The p159LART plasmid which was correctly constructed was used for the next step.

7. Construction of pYUOKLART Plasmid

As shown in FIG. 5, the pYUOK plasmid was digested with restriction endonuclease PacI, and a fragment of about 10.5 kb was recovered. The p159LART plasmid was digested with restriction endonuclease PacI, and a fragment of about 2 kb was recovered. The two functional fragments were ligated to obtain a pYUOKLART plasmid of about 12.6 kb. The *E. coli* competent cells DH5α were transformed with the pYUOKLART plasmid. Positive clones were screened using the LB solid plate with resistance to apramycin. A monoclone was picked and cultured in the LB liquid medium. Then the plasmid was extracted and then identified through an enzyme digestion. The pYUOKLART plasmid which was correctly constructed was used for the next step.

8. Construction of p159OK Phasmid

Figure 6:
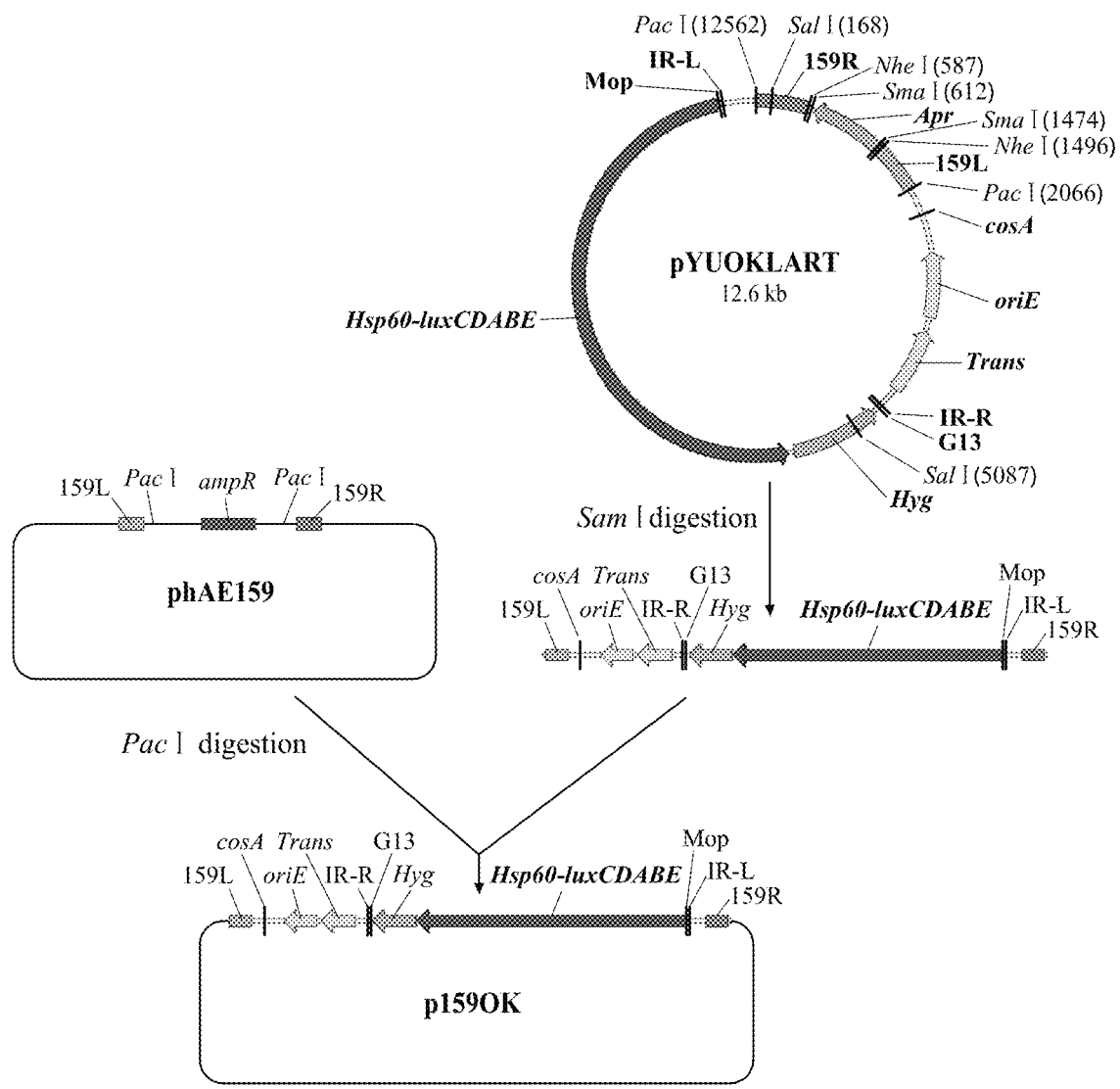

As shown in FIG. 6, a phAE159 phasmid (presented by Howard Hughes Medical Institute, USA) was digested with restriction endonuclease PacI, and the digested product was recovered with ethanol precipitation. The pYUOKLART plasmid was digested with restriction endonuclease SmaI, and the digested product was recovered with the ethanol precipitation. *E. coli* competent cells BJ5183 were transformed with a mixture of the two products to obtain a p159OK phasmid of 57 kb. Positive clones were screened using the LB solid plate with resistance to hygromycin and then the luminescence of the positive clone was detected. A monoclone was picked and cultured in the LB liquid medium, and the luminescence of bacterial suspension was detected. Then the phasmid was extracted from the luminescent bacterial suspension and then identified through an enzyme digestion. Two fragments of about 10.5 kb and 2.1 kb respectively can be digested from the correctly constructed p159OK phasmid.

Example 2 Preparation of a Phage Capable of Delivering Auto-Luminescent Elements 7H9 medium and Tween 80 involved in this embodiment were both purchased from Guangzhou Huaqisheng Biotech Co., Ltd. Agar was purchased from Guangzhou Kanglong Biotech Co., Ltd. Biorad electroporator (Biorad GenePpLser Xcell) and electroporation cuvette were purchased from Biorad Company.

Materials

1) *Mycobacterium smegmatis* MC$^2$155 (Msm) was provided by China General Microbiological Culture Collection Center (CGMCC), preservation No: 1.2621.

2) Top agar: 0.6% agar.

3) MP buffer: 50 mL of 1 M Tris-HCL (pH 7.5), 8.766 g of NaCl (final concentration of 150 mM), 2.46 g of magnesium sulfate heptahydrate (final concentration of 10 mM)

and 0.222 g of anhydrous calcium chloride (final concentration of 2 mM) were added to distilled water to a final volume of 1 L followed by a filtration to remove the bacteria.

Specifically, the processes are described in detail below.

Method for preparing the phage by electrotransformation 1) 10 μl of concentrated P159OK plasmid and 200 μl of Msm competent cells were added to a labeled electroporation cuvette (0.2 cm), and mixed gently and thoroughly. The cuvette was then placed on ice for 10 minutes. The moisture on the cuvette needed to be wiped off before inserting it into the electroporator.

2) Electrotransformation was performed using the electroporator with a pulse wave of 2.5 KY voltage, 1000Ω resistance and 25 μF capacitance. The pulse time of the negative bacteria control without plasmid should be between 19-21 seconds, at which the bacteria to be transformed were in a good state.

3) 2 mL of 7H9 medium (without Tween 80) was added into the electroporation solution, and then was transferred to a 50 mL centrifuge tube followed by an incubation in an incubator at 37° C. for 3 hours.

4) After the incubation, the system was centrifuged to obtain a precipitation and a supernatant which was discarded. The precipitation was resuspended with 150 μl of 7H9 medium (without Tween 80). 10 or 100 μl of the resuspended bacteria suspension was introduced to 3.5 mL of top agar cooled to 42° C., which then was applied on a solid LB medium plate. The plate was incubated in an incubator at 30° C. and plaques appeared after 48 hours, while some larger plaques appeared earlier than 48 hours.

5) 2 mL of MP buffer was added to each plate and the plate was shaken at 4° C. for several hours. Liquid from plates was filtered with a 0.4 μm filter to produce a filtrate and the filtrate containing phages was stored at 4° C.

Example 3 Method of Transposing DNA BY a Phage into a *Mycobacterium*

1) *Mycobacterium* was inoculated into a conical flask containing 50 mL of 7H9 liquid medium (containing 0.1% Tween 80), and then incubated under shaking at 37° C. to produce a bacterial suspend with 0D600 of 0.8-1.0.

2) 45 mL of the bacterial suspension was washed with an equal volume of NIP buffer. The washed bacterial suspension was centrifuged at 6000 rpm for 5 minutes to produce precipitation and supernatant which was discarded.

3) 5 mL of MP buffer was used to resuspend the precipitation, 200 μl of which was taken as a control.

4) About $10^9$ phages prepared above were added to the resuspension (or MP buffer as a control), and was incubated at 37° C. for 4-12 hours; wherein the volume of the phage was preferably less than 2 mL.

5) After the incubation, the sample was applied on a surface of 7H11 solid medium with resistance to hygromycin and was incubated at 37° C. Luminescent colonies on the medium were observed within about 3 days of incubation (*mycobacterium* of slow growth may require 3-4 weeks). Thus, the auto-luminescent colonies of *mycobacterium* mutated by transposon insertion were obtained.

Example 4 Application of the Phage in Detecting Mtb

Figure 7:
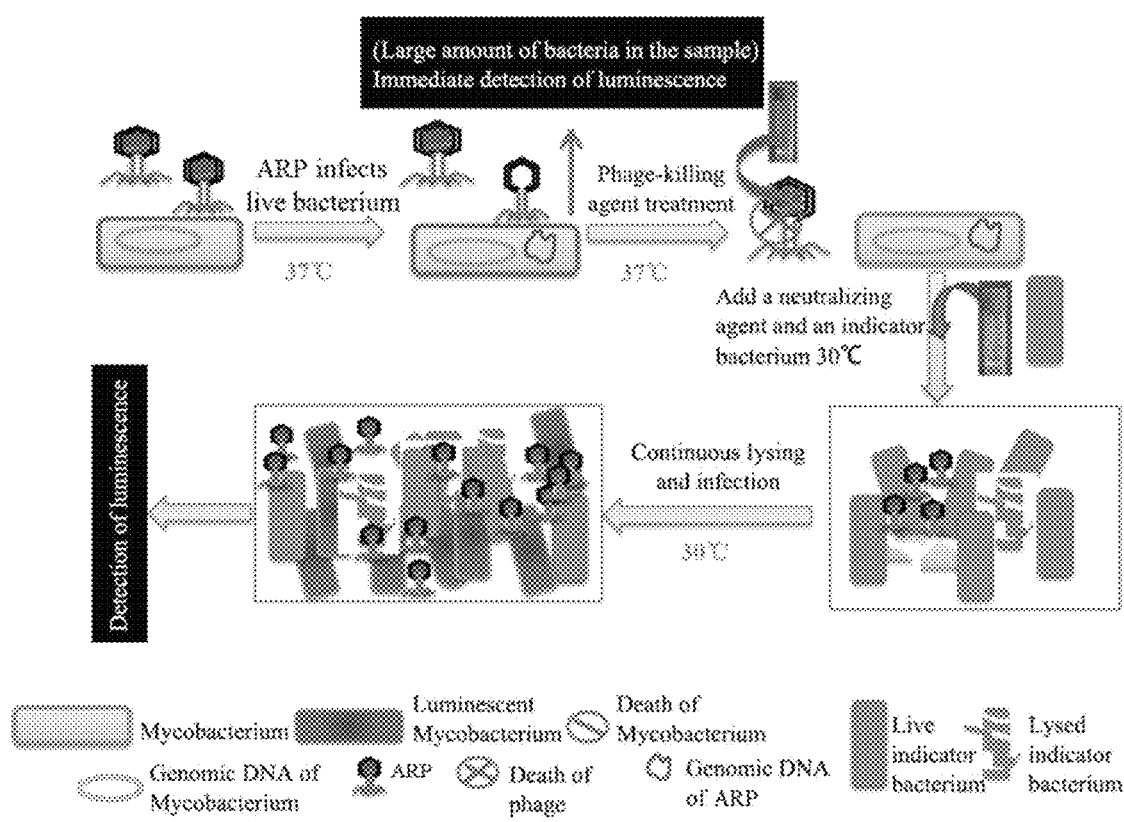

Method: a schematic diagram of detecting live *mycobacterium* (i.e., Mtb) in a sample was illustrated in FIG. 7.

1) A liquid containing a phage (ARP) was added to a sample to be detected.

2) A mixture of the sample and the liquid containing the phage was cultured at 37° C. for more than 35 minutes, and luminescence of the mixture was detected with a luminometer. The culture may be carried out at 36.5-42° C.

3) If significant bioluminescence was detected, the presence of a large amount of live mycobacteria in the sample was indicated; and if the bioluminescence intensity is lower than 120% of the bioluminescence intensity of the negative control, a phage-killing reagent SK was added to kill the phage failing to transpose its genome into *mycobacterium*. The SK reagent is selected from at least one of ammonium sulfate, ferrous sulfate, ammonia sulfate and ammonium ferrous sulfate, and these reagents were all purchased from Sigma Company.

4) A neutralizing agent SN was then added to neutralize the excess SK reagent, and an indicator bacterium (Msm) was added. The sample was incubated at 30° C. (may be 20-32° C.) for more than 12 hours. During the incubation, the phages inside *mycobacterium* of the sample lysed host cells, After being released, the phages can infect the indicator bacterium in a large amount and circulate the process of entering and lysing the host. When enough phages have entered enough indicator bacteria, the sample would become luminescent, indicating the presence of live *mycobacterium* in the sample.

The neutralizing agent SN was selected from at least one of $MgSO_4$, potassium dichromate, $CaCl_2$ and $MnCl_2$ (Sigma Company).

5) The luminescence of the sample with the indicator bacterium was detected with a luminometer. If the sample was luminescent, the presence of live *mycobacterium* in the sample was demonstrate& and if the sample was not luminescent, the absence of live *mycobacterium* in the sample was demonstrated.

Figure 8:
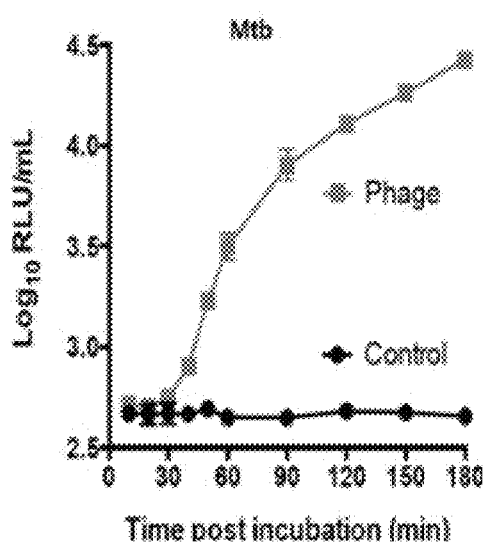

1. According to the method described above, the phages of the present invention were adopted to detect a sample containing more than $10^8$ Mtb. A liquid containing the phages was added to the sample to be detected and followed by a culture at 37° C. for 35 min. After the culture, a significant intensity of luminescence was detected with the luminometer when compared with a control, which indicated that the detection method of the present invention is fast and easy to operate. Furthermore, the luminescence intensity became stronger as the culture time extended (shown in FIG. 8).

Figure 9:
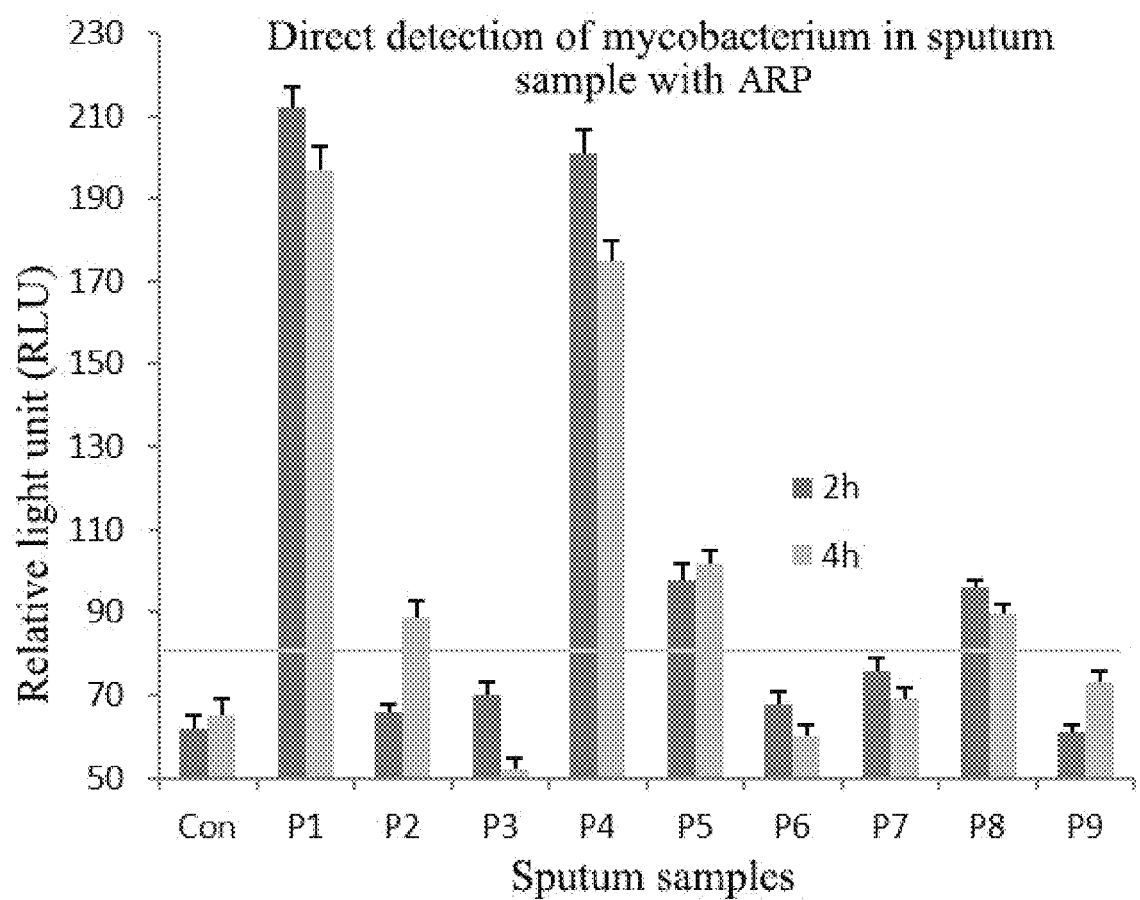

2. According to the method described above, the phages of the present invention were adopted to detect 9 positive clinical sputum samples (P1 to P9) and the results were shown in FIG. 9. According to the results, a liquid containing the phages was added to the samples to be detected and then cultured at 37° C. for 2 h. After the culture, samples P1, P4, P5 and P8 showed as positive and 4 hours later, sample P2 also showed as positive. However, a content of Mtb in other positive sputum samples was too small to be detected effectively in a short time (within 4 hours).

Figure 10:
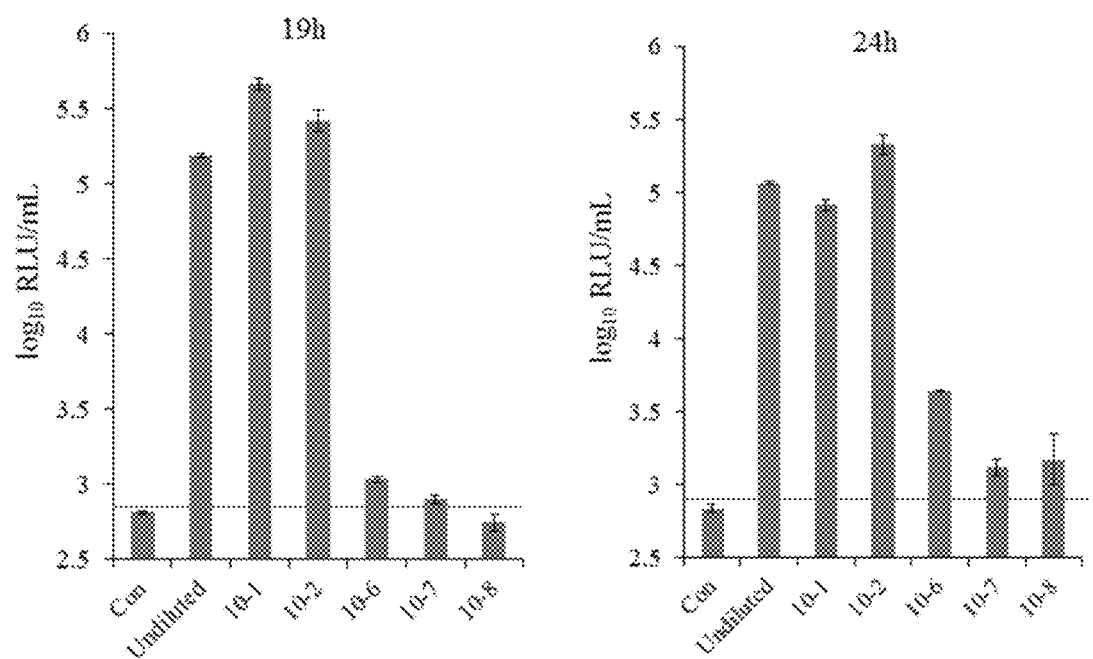

3. In order to further study a sensitivity of the above detection method, Mtb samples diluted with different times were detected. When diluted to $10^{-8}$, the amount of Mtb in each sample was not more than 10. The details referred to the method of Example 4, and after the phages were added the culture was carried out at 37° C. for 4 hours. The results were shown in FIG. 10. Less than 10 mycobacteria were detected in the samples after about 24 hours (the "24 hours" mentioned herein referred to the time after the addition of the indicator bacterium).

In summary, it can be seen that if there was a large amount of Mtb in the sample, Mtb can be quickly detected within 4 hours. If the amount of Mtb is small in the sample, less than 10 mycobacteria can be detected in the sample after about 28 hours.

Figure 11:
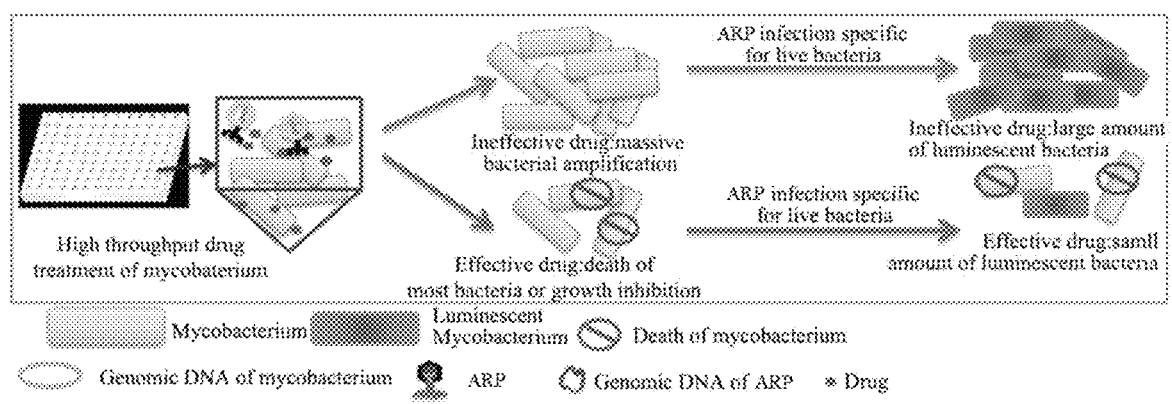

Example 5 Application of the Phage in Detecting Sensitivity of a Host Bacterial Strain to a Drug Method: a schematic diagram of detecting sensitivity of a host bacterial strain to a drug was illustrated in FIG. 11.

1) A phage (ARP) prepared by the present invent was mixed with target live bacteria (i.e., Mtb) contained in a 1.5 mL transparent tube (or a 96-well plate), and a drug of a concentration was added into the transparent tube.

2) They were cultured at 37° C. for at least 2 hours (the culture temperature may be 36.5-42° C.). After the culture, the luminescence was detected with a luminometer.

3) If there is a significant difference between the luminescence of the tested sample and that of a sample with no drug, the host bacteria is sensitive to the drug of the concentration; if there is no significant difference, the host bacteria is resistant to the drug at the concentration.

Figure 12:
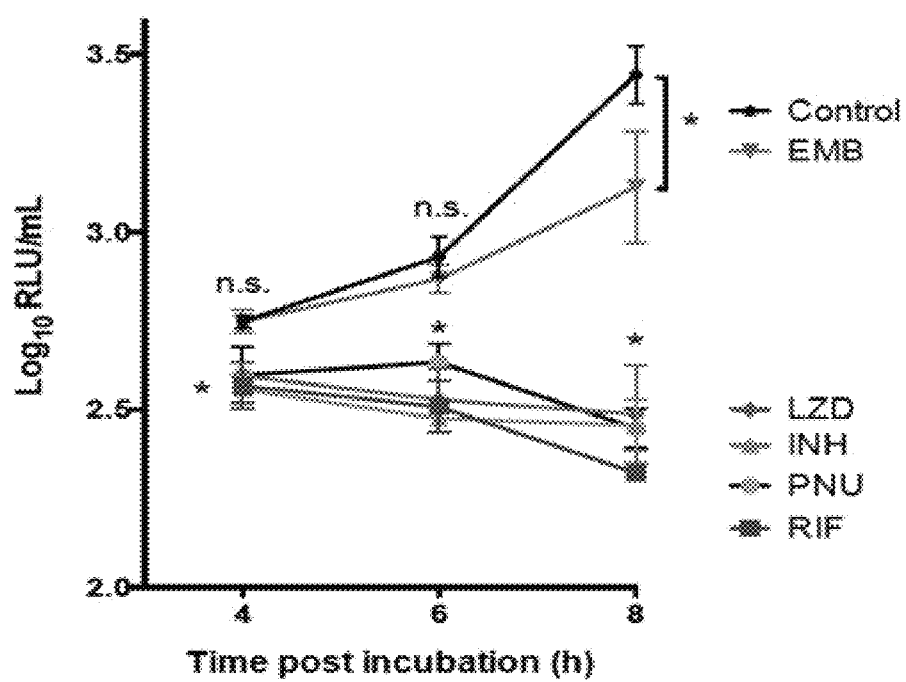
Figure 13:
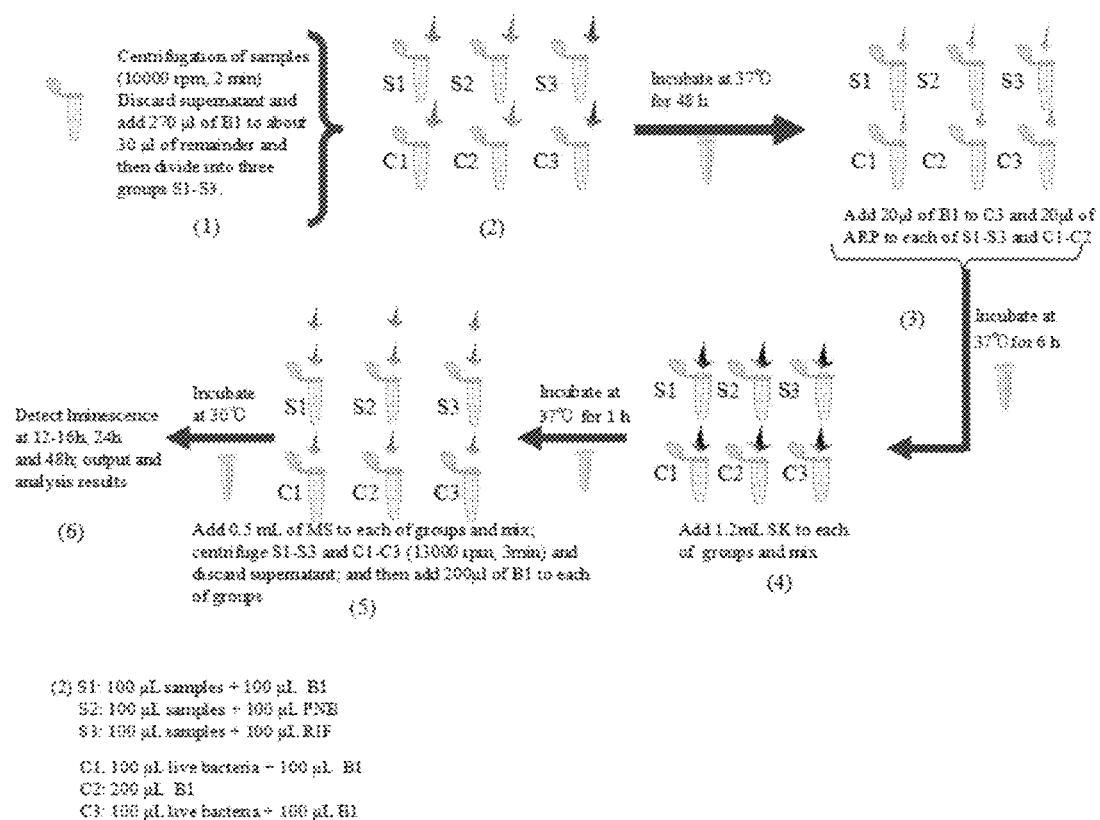

According to the method as described above, the sensitivity of Mtb to each of the following drugs was detected: rifampicin (RIF, 2 μg/mL), isoniazid (INH, 1 μg/mL), ethambutol (EMB, 5 μg/mL), linezolid (LZD, 1 μg/mL) and oxazolidinone (PNU, 0.5 μg/mL), and the results were shown in FIG. 12. As shown in FIG. 12, after a culture at 37° C. for at least 4 hours, significant decrease of biolumines- cence intensity was observed in the groups treated by rifampicin (RIF, 2 μg/mL), isoniazid (INH, 1 μg/mL), linezolid (LZD, 1 μg/mL) and oxazolidinone (PNU, 0.5 μg/mL) when compared to a control. Such results demonstrated sensitivities of Mtb to rifampicin (RIF, 2 μg/mL), isoniazid (INH, 1 μg/mL), linezolid (LZD, 1 μg/mL) and oxazolidinone (PNU, 0.5 μg/mL). A significant decrease in bioluminescence was also observed in a group treated by ethambutol (EMB, 5 μg/mL) after a culture for 8 hours, which indicated a sensitivity of Mtb to ethambutol (EMB, 5 μg/mL). FIG. 13 illustrates a process for detecting live mycobacteria in samples and sensitivity of the mycobacteria to RIF. RIF should be preserved at low temperature due to p-nitrobenzoic acid (PNB). As references, C1 emitted light, and C2-C3 did not emit light. Through such operation, the presence of live mycobacteria, and further live *Mycobacterium tuberculosis* in the samples, may be determined. Whether the bacteria was sensitive to RIF can be determined through the luminescence of PNB tube.

In summary, the method of the present invention can rapidly detect a sensitivity of a host bacterium (i.e., Mtb) to various drugs within 4-8 hours.

The above embodiments are preferred embodiments of the present invention, but the invention is not limited thereto. Any equivalent changes, modifications, substitutions, combinations, and simplifications that are made without departing from the spirit and principles of the invention are intended to fall within the scope of the present invention.

What is claimed is:

1. A phasmid enabling auto-luminescence of a host bacterium, wherein the phasmid comprises:
   the DNA sequence of SEQ ID NO: 1 capable of enabling auto-luminescence of the host bacterium.

2. A phage capable of delivering an auto-luminescent element, wherein the phage comprises the phasmid of claim 1.

* * * * *

SEQUENCE LISTING

```
<160> NUMBER OF SEQ ID NOS: 9

<210> SEQ ID NO 1
<211> LENGTH: 11648
<212> TYPE: DNA
<213> ORGANISM: Artificial Sequence
<220> FEATURE:
<223> OTHER INFORMATION: synthetic
<220> FEATURE:
<221> NAME/KEY: misc_feature
<222> LOCATION: (1031)..(1033)
<223> OTHER INFORMATION: n is a, c, g, or t
<220> FEATURE:
<221> NAME/KEY: misc_feature
<222> LOCATION: (1446)..(1448)
<223> OTHER INFORMATION: n is a, c, g, or t
<220> FEATURE:
<221> NAME/KEY: misc_feature
<222> LOCATION: (7270)..(7272)
<223> OTHER INFORMATION: n is a, c, g, or t

<400> SEQUENCE: 1
gctagcccgg cctgccgccg atccccgaca ccgacgacgt gtgcaaggcc cttggcatca      60
aggcccgcac gacgctgcac aacgtgcttt accgtcaccg tgacgaaatg atcgcgggcg     120
gatgggacgc cgccgcaggc acattcacgc gcgaggccgt tgtgcggctg tgcctgctgc     180
tgcgcgccac cacctcgcgc aaggcggccg aagtcgccga ggcggtcggc gcccgcgatc     240
gcgtgatcaa gttcaacgcc agcaaggtgc cgcacattcg gcgctgccag gcgttgatag     300
acaaggcatt cggccttgct gagcgcgtgc gcgacgaaga tcccgccgag gtgtggcacg     360
acctcaatca gatggacgcc tacacgctgc agggcatcac cgtggccctg gcggcgatgg     420
tcgacctcga ctcggcgacc ggcggtgtga cgcagtggct tagctcgctg gcccgtcta     480 agcggcaccc cggcaagggc aacggcggcg ccgcgagcgg tttggcccgg ctggtgccga     540
cacccgatga ggcgcagggc atcccgctgg gcaagatcct gatcaggcgc cttaattaag     600
```

```
atcctttagt gagggttaat tgcggccgcg aattcttgaa gacgaaaggg cctcgtgata      660
cgcctatttt tataggttaa tgtcatgaaa tatttgctta tacaatcttc ctgttttgg      720 ggcttttctg attatcaacc ggggtaaatc aatctaaagt atatatgagt aaacttggtc      780
tgacagttac caatgcttaa tcagtgaggc acctatctca gcgatctgtc tatttcgttc      840
atccatagtt gcctgactcc cagtccgtaa tacgactcac ttaaggcctt gactagaggg      900
taccagagct cacctaggta tctagttaac aggttggctg ataagtcccc ggtctggatc      960
cgaattgtga gcgctcacaa ttccacacat tatacgagcc ggaagcataa agtgtcaagc     1020
ctggggtacc nnntctagag gtgaccacaa cgacgcgccc gctttgatcg gggacgtctg     1080
cggccgacca tttacgggtc ttgttgtcgt tggcggtcat gggccgaaca tactcacccg     1140
gatcggaggg ccgaggacaa ggtcgaacga ggggcatgac ccggtgcggg gcttcttgca     1200
ctcggcatag gcgagtgcta agaataacgt tggcactcgc gaccggtgag tcgtaggtcg     1260
ggacggtgag gccaggcccg tcgtcgcagc gagtggcagc gaggacaact tgagccgtcc     1320
gtcgcgggca ctgcgcccgg ccagcgtaag tagcggggtt gccgtcaccc ggtgaccccc     1380
ggtttcatcc ccgatcctca cttcggagga atcacttcgc aatggccaag acaattgcgg     1440
gatccnnnga attcaggctt ggaggatacg tatgactaaa aaaatttcat tcattattaa     1500
cggccaggtt gaaatctttc ccgaaagtga tgatttagtg caatccatta attttggtga     1560
taatagtgtt tacctgccaa tattgaatga ctctcatgta aaaaacatta ttgattgtaa     1620
tggaaataac gaattacggt tgcataacat tgtcaatttt ctctatacgg tagggcaaag     1680
atggaaaaat gaagaatact caagacgcag gacatacatt cgtgacttaa aaaaatatat     1740
gggatattca gaagaaatgg ctaagctaga ggccaattgg atatctatga ttttatgttc     1800
taaaggcggc ctttatgatg ttgtagaaaa tgaacttggt tctcgccata tcatggatga     1860
atggctacct caggatgaaa gttatgttcg ggcttttccg aaaggtaaat ctgtacatct     1920
gttggcaggt aatgttccat tatctgggat catgtctata ttacgcgcaa ttttaactaa     1980
gaatcagtgt attataaaaa catcgtcaac cgatcctttt accgctaatg cattagcgtt     2040
aagttttatt gatgtagacc ctaatcatcc gataacgcgc tctttatctg ttatatattg     2100 gcccaccaa ggtgatacat cactcgcaaa agaaattatg cgacatgcgg atgttattgt     2160
cgcttgggga gggccagatg cgattaattg ggcggtagag catgcgccat cttatgctga     2220
tgtgattaaa tttggttcta aaaagagtct ttgcattatc gataatcctg ttgatttgac     2280
gtccgcagcg acaggtgcgg ctcatgatgt ttgtttttac gatcagcgag cttgttttc      2340 tgcccaaaac atatattaca tgggaaatca ttatgaggaa tttaagttag cgttgataga     2400
aaaacttaat ctatatgcgc atatattacc gaatgccaaa aaagattttg atgaaaaggc     2460
ggcctattct ttagttcaaa agaaagcttt gtttgctgga ttaaaagtag aggtggatat     2520
tcatcaacgt tggatgatta ttgagtcaaa tgcaggtgtg gaatttaatc aaccacttgg     2580
cagatgtgtg taccttcatc acgtcgataa tattgagcaa atattgcctt atgttcaaaa     2640
aaataagacg caaaccatat ctatttttcc ttgggagtca tcatttaaat atcgagatgc     2700
gttagcatta aaaggtgcgg aaaggattgt agaagcagga atgaataaca tatttcgagt     2760
tggtggatct catgacggaa tgagaccgtt gcaacgatta gtgacatata tttctcatga     2820
aaggccatct aactatacgg ctaaggatgt tgcggttgaa atagaacaga ctcgattcct     2880
ggaagaagat aagttccttg tatttgtccc ataataggta aaagtatgga aaatgaatca     2940
```

```
aaatataaaa ccatcgacca cgttatttgt gttgaaggaa ataaaaaaat tcatgtttgg    3000
gaaacgctgc cagaagaaaa cagcccaaag agaaagaatg ccattattat tgcgtctggt    3060
tttgcccgca ggatggatca ttttgctggt ctggcggaat atttatcgcg gaatggattt    3120
catgtgatcc gctatgattc gcttcaccac gttggattga gttcagggac aattgatgaa    3180
tttacaatgt ctataggaaa gcagagcttg ttagcagtgg ttgattggtt aactacacga    3240
aaaataaata acttcggtat gttggcttca agcttatctg cgcggatagc ttatgcaagc    3300
ctatctgaaa tcaatgcttc gttttaatc accgcagtcg gtgttgttaa cttaagatat     3360
tctcttgaaa gagctttagg gtttgattat ctcagtctac ccattaatga attgccggat    3420
aatctagatt ttgaaggcca taaattgggt gctgaagtct ttgcgagaga ttgtcttgat    3480
tttggttggg aagatttagc ttctacaatt aataacatga tgtatcttga tataccgttt    3540
attgctttta ctgcaaataa cgataattgg gtcaagcaag atgaagttat cacattgtta    3600
tcaaatattc gtagtaatcg atgcaagata tattctttgt taggaagttc gcatgacttg    3660
agtgaaaatt tagtggtcct gcgcaatttt tatcaatcgg ttacgaaagc cgctatcgcg    3720
atggataatg atcatctgga tattgatgtt gatattactg aaccgtcatt tgaacattta    3780
actattgcga cagtcaatga acgccgaatg agaattgaga ttgaaaatca agcaatttct    3840
ctgtcttaaa atctattgag atattctatc actcaaatag caatataagg actctctatg    3900
aaatttggaa actttttgct tacataccaa cctcccccaat tttctcaaac agaggtaatg   3960
aaacgtttgg ttaaattagg tcgcatctct gaggagtgtg gttttgatac cgtatggtta    4020
ctggagcatc atttcacgga gtttggtttg cttggtaacc cttatgtcgc tgctgcatat    4080
ttacttggcg cgactaaaaa attgaatgta ggaactgccg ctattgttct tcccacagcc    4140
catccagtac gccaacttga agatgtgaat ttattggatc aaatgtcaaa aggacgattt    4200
cggtttggta tttgccgagg gctttacaac aaggactttc gcgtattcgg cacagatatg    4260
aataacagtc gcgccttagc ggaatgctgg tacgggctga taagaatgg catgacagag     4320 ggatatatgg aagctgataa tgaacatatc aagttccata aggtaaaagt aaaccccgcg    4380
gcgtatagca gaggtggcgc accggtttat gtggtggctg aatcagcttc gacgactgag    4440
tgggctgctc aatttggcct accgatgata ttaagttgga ttataaatac taacgaaaag    4500
aaagcacaac ttgagcttta taatgaagtg gctcaagaat atgggcacga tattcataat    4560
atcgaccatt gcttatcata tataacatct gtagatcatg actcaattaa agcgaaagag    4620
atttgccgga aatttctggg gcattggtat gattcttatg tgaatgctac gactattttt    4680
gatgattcag accaaacaag aggttatgat ttcaataaag ggcagtggcg tgactttgta    4740
ttaaaaggac ataagataca taatcgccgt attgattaca gttacgaaat caatcccgtg    4800
ggaacgccgc aggaatgtat tgacataatt caaaaagaca ttgatgctac aggaatatca    4860
aatatttgtt gtggatttga agctaatgga acagtagacg aaattattgc ttccatgaag    4920
ctcttccagt ctgatgtcat gccatttctt aaagaaaaac aacgttcgct attatattag    4980
ctaaggagaa agaaatgaaa tttggattgt tcttccttaa cttcatcaat tcaacaactg    5040
ttcaagaaca agtatagtt cgcatgcagg aaataacgga gtatgttgat aagttgaatt     5100
ttgaacagat tttagtgtat gaaaatcatt tttcagataa tggtgttgtc ggcgctcctc    5160
tgactgtttc tggttttctg ctcggttaa cagagaaaat taaaattggt tcattaaatc     5220
acatcattac aactcatcat cctgtcgcca tagcggagga agcttgctta ttggatcagt    5280
taagtgaagg gagatttatt ttagggttta gtgattgcga aaaaaaagat gaaatgcatt    5340
```

```
tttttaatcg cccggttgaa tatcaacagc aactatttga agagtgttat gaaatcatta    5400
acgatgcttt aacaacaggc tattgtaatc cagataacga tttttatagc ttccctaaaa    5460
tatctgtaaa tccccatgct tatacgccag gcggacctcg gaaatatgta acagcaacca    5520
gtcatcatat tgttgagtgg gcggccaaaa aaggtattcc tctcatcttt aagtgggatg    5580
attctaatga tgttagatat gaatatgctg aaagatataa agccgttgcg gataaatatg    5640
acgttgacct atcagagata gaccatcagt taatgatatt agttaactat aacgaagata    5700
gtaataaagc taaacaagag acgcgtgcat ttattagtga ttatgttctt gaaatgcacc    5760
ctaatgaaaa tttcgaaaat aaacttgaag aaataattgc agaaaacgct gtcggaaatt    5820
atacggagtg tataactgcg gctaagttgg caattgaaaa gtgtggtgcg aaaagtgtat    5880
tgctgtcctt tgaaccaatg aatgatttga tgagccaaaa aaatgtaatc aatattgttg    5940
atgataatat taagaagtac cacatggaat atacctaata gatttcgagt tgcagcgagg    6000
cggcaagtga acgaatcccc aggagcatag ataactatgt gactggggtg agtgaaagca    6060
gccaacaaag cagcagcttg aaagatgaag ggtataaaag agtatgacag cagtgctgcc    6120
atactttcta atattatctt gaggagtaaa acaggtatga cttcatatgt tgataaacaa    6180
gaaattacag caagctcaga aattgatgat ttgattttttt cgagcgatcc attagtgtgg    6240
tcttacgacg agcaggaaaa aatcagaaag aaacttgtgc ttgatgcatt tcgtaatcat    6300
tataaacatt gtcgagaata tcgtcactac tgtcaggcac acaaagtaga tgacaatatt    6360
acggaaattg atgacatacc tgtattccca acatcggttt ttaagtttac tcgcttatta    6420
acttctcagg aaaacgagat tgaaagttgg tttaccagta gcggcacgaa tggtttaaaa    6480
agtcaggtgg cgcgtgacag attaagtatt gagagactct taggctctgt gagttatggc    6540
atgaaatatg ttggtagttg gtttgatcat caaatagaat tagtcaattt gggaccagat    6600
agatttaatg ctcataatat ttggtttaaa tatgttatga gtttggtgga attgttatat    6660
cctacgacat ttaccgtaac agaagaacga atagattttg ttaaaacatt gaatagtctt    6720
gaacgaataa aaaatcaagg gaaagatctt tgtcttattg gttcgccata ctttatttat    6780
ttactctgcc attatatgaa agataaaaaa atctcatttt ctggagataa aagcctttat    6840
atcataaccg gaggcggctg gaaaagttac gaaaagaat ctctgaaacg tgatgatttc    6900
aatcatcttt tatttgatac tttcaatctc agtgatatta gtcagatccg agatatattt    6960
aatcaagttg aactcaacac ttgtttcttt gaggatgaaa tgcagcgtaa acatgttccg    7020
ccgtgggtat atgcgcgagc gcttgatcct gaaacgttga aacctgtacc tgatggaacg    7080
ccggggttga tgagttatat ggatgcgtca gcaaccagtt atccagcatt tattgttacc    7140
gatgatgtcg ggataattag cagagaatat ggtaagtatc ccggcgtgct cgttgaaatt    7200
ttacgtcgcg tcaatacgag gacgcagaaa gggtgtgctt taagcttaac cgaagcgttt    7260
gatagttgan nnctcgagtc tagaccggcc gtgcggaatt aagccggccc gtaccctgtg    7320
aatagaggtc cgctgtgaca caagaatccc tgttacttct cgaccgtatt gattcggatg    7380
attcctacgc gagcctgcgg aacgaccagg agttctggga ccgctggcc cgccgagccc    7440
tggaggagct cgggctgccg gtgccgccgg tgctgcgggt gccggcgag agcaccaacc    7500
ccgtactggt cggcgagccc ggcccggtga tcaagctgtt cggcgagcac tggtgcggtc    7560
cggagagcct cgcgtcggag tcggaggcgt acgcggtcct ggcggacgcc ccggttccgg    7620
tgccccgcct cctcggccgc ggcgagctgc ggcccggcac cggagcctgg ccgtggccct    7680
```

```
acctggtgat gagccggatg accggcacca cctggcggtc cgcgatggac ggcacgaccg    7740
accggaacgc gctgctcgcc ctggcccgcg aactcggccg ggtgctcgga cggctgcaca    7800
gggtgccgct gaccgggaac accgtgctca ccccccattc cgaggtcttc ccggaactgc    7860
tgcgggaacg ccgcgcggcg accgtcgagg accaccgcgg gtggggctac ctctcgcccc    7920
ggctgctgga ccgcctggag gactggctgc cggacgtgga cacgctgctg gccggccgcg    7980
aaccccggtt cgtccacggc gacctgcacg ggaccaacat cttcgtggac ctggccgcga    8040
ccgaggtcac cgggatcgtc gacttcaccg acgtctatgc gggagactcc cgctacagcc    8100
tggtgcaact gcatctcaac gccttccggg gcgaccgcga gatcctggcc gcgctgctcg    8160
acggggcgca gtggaagcgg accgaggact cgcccgcga actgctcgcc ttcaccttcc    8220
tgcacgactt cgaggtgttc gaggagaccc cgctggatct ctccggcttc accgatccgg    8280
aggaactggc gcagttcctc tgggggccgc cggacaccgc ccccggcgcc tgatctagat    8340
tgcagaactt tcatgaatta ggccttgctg cgcccaggct ccagtagtag aaatggagtc    8400
acggcagaga ccgggagctt atcagccaac ctgttaccgt ccagtctggc aggccggaac    8460
atcggtcagc agataggctt taccagtaag aaggagatat accatggatg ttgataaaat    8520
actgttttct gaagggaaaa aatacggtgg aagcaaaaac ttggcttgat aatgagtttc    8580
cggactctgc cccagggaaa tcaacaataa ttgattggta tgcaaaattc aagcgtggtg    8640
aaatgagcac ggaggacggt gaacgcagtg gacgccgaa agaggtggtt accgacgaaa    8700
acatcaaaaa aatccacaaa atgatttga atgaccgtaa aatgaagtta atcgagatag    8760
cagaggcctt aaagatatca aaggaacgtg ttggtcatat cattcatcaa tatttggata    8820
tgcggaagct ctgtgcaaaa tgggtgccgc gcgagctcac atttgaccaa aaacaacgac    8880
gtgttgatga ttctaagcgg tgtttgcagc tgttaactcg taatacaccc gagttttcc    8940 gtcgatatgt gacaatggat gaaacatggc tccatcacta cactcctgag tccaatcgac    9000
agtcggctga gtggacagcg accggtgaac cgtctccgaa gcgtggaaag actcaaaagt    9060
ccgctggcaa agtaatggcc tctgtttttt gggatgcgca tggaataatt tttatcgatt    9120
atcttgagaa gggaaaaacc atcaacagtg actattatat ggcgttattg gagcgtttga    9180
aggtcgaaat cgcggcaaaa cggccccaca tgaagaagaa aaaagtgttg ttccaccaag    9240
acaacgcacc gtgccacaag tcattgagaa cgatggcaaa aattcatgaa ttgggcttcg    9300
aattgcttcc ccacccaccg tattctccag atctggcccc cagcgacttt tcttgttct    9360 cagacctcaa aaggatgctc gcagggaaaa aatttggctg caatgaagag gtgatcgccg    9420
aaactgaggc ctattttgag gcaaaaccga aggagtacta ccaaaatggt atcaaaaaat    9480
tggaaggtcg ttataatcgt tgtatcgctc ttgaagggaa ctatgttgaa taaactagtg    9540
agtcgtatta ccatgaccaa aatcccttaa cgtgagtttt cgttcgactg agcgtcagac    9600
cccgtagaaa atatcaaagg atcttcttga gatcctttt ttctgcgcgt aatctgctgc    9660
ttgcaaacaa aaaaaccacc gctaccagcg gtggtttgtt tgccggatca agagctacca    9720 actcttttc cgaaggtaac tggcttcagc agagcgcaga taccaaatac tgtccttcta    9780
gtgtagccgt agttaggcca ccacttcaag aactctgtag caccgcctac atacctcgct    9840
ctgctaatcc tgttaccagt ggctgctgcc agtggcgata agtcgtgtct taccgggttg    9900
gactcaagac gatagttacc ggataaggcg cagcggtcgg gctgaacggg gggttcgtgc    9960
acacagccca gcttggagcg aacgacctac accgaactga atacctaca gcgtgagcta   10020 tgagaaagcg ccacgcttcc cgaagggaga aaggcggaca ggtatccggt aagcggcagg   10080
```

```
gtcggaacag gagagcgcac gagggagctt ccaggggggaa acgcctggta tctttatagt    10140
cctgtcgggt ttcgccacct ctgacttgag cgtcgatttt tgtgatgctc gtcagggggg    10200
cggagcctat ggaaaaacgc cagcaacgcg gcctttttac ggttcctggc cttttgctgg    10260
ccttttgctg gccttttgct cacatgttct ttcctgcgtt atcccctgat tctgtggata    10320
accgtattac cgcctttgag tgagctgata ccgctcgccg cagccgaacg accgagcgca    10380
gcgagtcagt gagcgaggaa gcggaagagc gctgacttcc gcgtttccag actttacgaa    10440
acacggaaac cgaagaccat tcatgttgtt gctcaggtcg cagacgtttt gcagcagcag    10500
tcgcttcacg ttcgctcgcg tatcggtgat tcattctgct aaccagtaag caaccccgc     10560 cagcctagcc gggtcctcaa cgacaggagc acgatcatgc gcacccgtca gatccagaca    10620
tgataagata cattgatgag tttggacaaa ccacaactag aatgcagtga aaaaaatgct    10680
ttatttgtga aatttgtgat gctattgctt tatttgtaac cattataagc tgcaataaac    10740
aagttcgcga attgataatt attatcattt gcgggtcctt tccggcgatc cgccttgtta    10800
cggggcggcg acctcgcggg ttttcgctat ttatgaaaat tttccggttt aaggcgtttc    10860
cgttcttctt cgtcataact taatgttttt atttaaaata ccctctgaaa agaaaggaaa    10920
cgacaggtgc tgaaagcgag cttttttggcc tctgtcgttt cctttctctg ttttttgtccg    10980 tggaatgaac aatggaagtc aacaaaaagc agagcttatc gatgataagc ggtcaaacat    11040
gagaattcgc ggccgcataa tacgactcac tatagggatc ttaattaagg atcgcgaagg    11100
cgacgcagcg cgtgcagcag cggcagatcg ggctgctgac gacgcagcgc gagattatcg    11160
acgaccagct cgccgacgcg gtgcgcaagc gcaacgaggc cagcggcctg attgcgcagg    11220
ctttgggcat gttgaacgct caacagtgag cactcggcat gaccgttatc gctgaataca    11280
tctaggcgca tagacatagc agcgtgcctc accacaactg ccccggcgac gactgcggtc    11340
gttgcgaggc gcgcattgcg gcgatcgagt acgagcgcga ggtcgcgcac gacgattacc    11400
cgcagttcta cgacggcacc tagagccccg cgggcgctcg cgcgggaatc cacaacgggc    11460
gcaaatgatc acgaaggaaa cacaggaaca catgagcaac gattcgtacg gattcctcgc    11520
aggcggcggc ccggcgtcgg gcaagttcaa ggcccacggc gacaccgtcg gcggcccgat    11580
cgtcgtcgag ccctcgcagc agcagcagac caacatggac aacaagccgc tgacctggga    11640
cgacggca                                                             11648

<210> SEQ ID NO 2
<211> LENGTH: 210
<212> TYPE: DNA
<213> ORGANISM: Artificial Sequence
<220> FEATURE:
<223> OTHER INFORMATION: synthetic

<400> SEQUENCE: 2
aagcttacta gtggtaccct gcagctcgag tctagattgc agaactttca tgaattaggc     60
cttgctgcgc ccaggctcca gtagtagaaa tggagtcacg gcagagaccg gggacttatc    120
agccaacctg ttaccgtcca gtctggcagg ccggaacatc ggtcagcaga taggctttac    180
cagtaagaag gagatatacc atgggaattc                                     210

<210> SEQ ID NO 3
<211> LENGTH: 151
<212> TYPE: DNA
<213> ORGANISM: Artificial Sequence
<220> FEATURE:
```

<223> OTHER INFORMATION: synthetic

<400> SEQUENCE: 3

```
aagcttacta gttaacaggt tggctgataa gtccccggtc tggatccgaa ttgtgagcgc    60
tcacaattcc acacattata cgagccggaa gcataaagtg tcaagcctgg ggtacctgac   120
gacaggaaga gttgtgtacc catgggaatt c                                  151
```

<210> SEQ ID NO 4
<211> LENGTH: 1167
<212> TYPE: DNA
<213> ORGANISM: Artificial Sequence
<220> FEATURE:
<223> OTHER INFORMATION: synthetic

<400> SEQUENCE: 4

```
ttaattaagg atcgcgaagg cgacgcagcg cgtgcagcag cggcagatcg ggctgctgac    60
gacgcagcgc gagattatcg acgaccagct cgccgacgcg gtgcgcaagc gcaacgaggc   120
cagcggcctg attgcgcagg ctttgggcat gttgaacgct caacagtgag cactcggcat   180
gaccgttatc gctgaataca tctaggcgca tagacatagc agcgtgcctc accacaactg   240
ccccggcgac gactgcggtc gttgcgaggc gcgcattgcg gcgatcgagt acgagcgcga   300
ggtcgcgcac gacgattacc gcagttcta cgacggcacc tagagccccg cgggcgctcg   360
cgcgggaatc cacaacgggc gcaaatgatc acgaaggaaa cacaggaaca catgagcaac   420
gattcgtacg gattcctcgc aggcggcggc ccggcgtcgg gcaagttcaa ggcccacggc   480
gacaccgtcg gcggcccgat cgtcgtcgag ccctcgcagc agcagcagac caacatggac   540
aacaagccgc tgacctggga cgacggcagc tagcccggcc tgccgccgat ccccgacacc   600
gacgacgtgt gcaaggccct tggcatcaag gcccgcacga cgctgcacaa cgtgctttac   660
cgtcaccgtg acgaaatgat cgcgggcgga tgggacgccg ccgcaggcac attcacgcgc   720
gaggccgttg tgcggctgtg cctgctgctg cgcgccacca cctcgcgcaa ggcggccgaa   780
gtcgccgagg cggtcggcgc ccgcgatcgc gtgatcaagt tcaacgccag caaggtgccg   840
cacattcggc gctgccaggc gttgatagac aaggcattcg gccttgctga gcgcgtgcgc   900
gacgaagatc ccgccgaggt gtggcacgac ctcaatcaga tggacgccta cacgctgcag   960
ggcatcaccg tggccctggc ggcgatggtc gacctcgact cggcgaccgg cggtgtgacg  1020
cagtggctta gctcgctggc cccgtctaag cggcaccccg gcaagggcaa cggcggcgcc  1080
gcgagcggtt tggcccggct ggtgccgaca cccgatgagg cgcagggcat cccgctgggc  1140
aagatcctga tcaggcgcct taattaa                                     1167
```

<210> SEQ ID NO 5
<211> LENGTH: 31
<212> TYPE: DNA
<213> ORGANISM: Artificial Sequence
<220> FEATURE:
<223> OTHER INFORMATION: synthetic

<400> SEQUENCE: 5

```
tgtccatgga tgttgataaa atactgtttt c                                  31
```

<210> SEQ ID NO 6
<211> LENGTH: 29
<212> TYPE: DNA
<213> ORGANISM: Artificial Sequence
<220> FEATURE:
<223> OTHER INFORMATION: synthetic

<400> SEQUENCE: 6
cctactagtt tattcaacat agttccctt                                     29

<210> SEQ ID NO 7
<211> LENGTH: 49
<212> TYPE: DNA
<213> ORGANISM: Artificial Sequence
<220> FEATURE:
<223> OTHER INFORMATION: synthetic

<400> SEQUENCE: 7
ctagctagcc ccgggagatc tgttaacgat atccaccacc gactatttg               49

<210> SEQ ID NO 8
<211> LENGTH: 49
<212> TYPE: DNA
<213> ORGANISM: Artificial Sequence
<220> FEATURE:
<223> OTHER INFORMATION: synthetic

<400> SEQUENCE: 8
ctagctagcc ccggggttaa cagatctgat atcagctcag ccaatcgac               49

<210> SEQ ID NO 9
<211> LENGTH: 1026
<212> TYPE: DNA
<213> ORGANISM: Artificial Sequence
<220> FEATURE:
<223> OTHER INFORMATION: synthetic

<400> SEQUENCE: 9
atgttgataa atactgtttt tctgaaggga aaaaatacgg tggaagcaaa aacttggctt    60
gataatgagt ttccggactc tgccccaggg aaatcaacaa taattgattg gtatgcaaaa   120
ttcaagcgtg gtgaaatgag cacggaggac ggtgaacgca gtggacgccc gaaagaggtg   180
gttaccgacg aaaacatcaa aaaaatccac aaaatgattt tgaatgaccg taaaatgaag   240
ttgatcgaga tagcagaggc cttaaagata tcaaaggaac gtgttggtca tatcattcat   300
caatatttgg atatgcggaa gctctgtgca aaatgggtgc cgcgcgagct cacatttgac   360
caaaaacaac gacgtgttga tgattctaag cggtgtttgc agctgttaac tcgtaataca   420
cccgagtttt tccgtcgata tgtgacaatg gatgaaacat ggctccatca ctacactcct   480
gagtccaatc gacagtcggc tgagtggaca gcgaccggtg aaccgtctcc gaagcgtgga   540
aagactcaaa agtccgctgg caaagtaatg gcctctgttt tttgggatgc gcatggaata   600
atttttatcg attatcttga aagggaaaaa ccatcaaca gtgactatta tatggcgtta   660
ttggagcgtt tgaaggtcga atcgcggca aaacggcccc acatgaagaa gaaaaaagtg   720
ttgttccacc aagacaacgc accgtgccac aagtcattga aacgatggc aaaaattcat   780 gaattgggct tcgaattgct tcccccaccca ccgtattctc cagatctggc ccccagcgac   840 ttttcttgt tctcagacct caaaaggatg ctcgcaggga aaaatttgg ctgcaatgaa    900 gaggtgatcg ccgaaactga ggcctatttt gaggcaaaac cgaaggagta ctaccaaaat   960
ggtatcaaaa aattggaagg tcgttataat cgttgtatcg ctcttgaagg gaactatgtt  1020
gaataa                                                            1026